United States Patent
Hersh

(10) Patent No.: US 7,207,804 B2
(45) Date of Patent: Apr. 24, 2007

(54) APPLICATION OF MULTI-MEDIA TECHNOLOGY TO COMPUTER ADMINISTERED VOCATIONAL PERSONNEL ASSESSMENT

(76) Inventor: Michael Hersh, 817-A Ave. M, Brooklyn, NY (US) 11230

(*) Notice: Subject to any disclaimer, the term of this patent is extended or adjusted under 35 U.S.C. 154(b) by 543 days.

(21) Appl. No.: 10/101,227

(22) Filed: Mar. 18, 2002

(65) Prior Publication Data
US 2002/0106617 A1    Aug. 8, 2002

Related U.S. Application Data

(63) Continuation-in-part of application No. 09/395,548, filed on Sep. 11, 1999, now Pat. No. 6,491,525, which is a continuation of application No. 08/829,488, filed on Mar. 27, 1997, now Pat. No. 6,030,226.

(60) Provisional application No. 60/277,140, filed on Mar. 19, 2001, provisional application No. 60/014,203, filed on Mar. 27, 1996.

(51) Int. Cl.
G09B 19/00    (2006.01)

(52) U.S. Cl. ............ 434/236; 434/219; 434/350; 434/323; 434/362

(58) Field of Classification Search ............ 434/29, 434/30, 61, 62, 156, 157, 218, 219, 236, 434/322, 323, 118, 258, 362, 365, 350; 706/FOR. 119; 700/90; 600/301; 705/2, 7, 10, 11
See application file for complete search history.

(56) References Cited

U.S. PATENT DOCUMENTS

| | | | |
|---|---|---|---|
| 3,390,397 A | 6/1968 | Friedlander | |
| 3,808,705 A | 5/1974 | Schmayer | 35/6 |
| 4,234,933 A | 11/1980 | Adelson et al. | 364/900 |
| 4,375,080 A | 2/1983 | Barry et al. | 364/551 |
| 4,490,810 A | 12/1984 | Hon | 364/900 |
| 4,627,818 A | 12/1986 | Von Fellenberg | 434/236 |
| 4,671,772 A * | 6/1987 | Slade et al. | 434/219 |
| 4,683,891 A * | 8/1987 | Cornellier et al. | 600/301 |
| 4,684,349 A | 8/1987 | Ferguson et al. | |
| 4,690,644 A | 9/1987 | Flanders et al. | |
| 4,690,645 A | 9/1987 | Ukisu | |
| 4,760,390 A | 7/1988 | Maine et al. | 340/747 |
| 4,770,636 A | 9/1988 | Buschke | 434/236 |
| 4,793,810 A | 12/1988 | Beasley, Jr. | 434/165 |

(Continued)

FOREIGN PATENT DOCUMENTS

EP    0 272 158    12/1987

(Continued)

*Primary Examiner*—Joe H. Cheng
(74) *Attorney, Agent, or Firm*—Alfred M. Walker; Frank Tolin

(57) ABSTRACT

A multi-media method and system performs psychological assessment of an individual for suitability for particular jobs, whereby the individual is shown and provided with discrete visual and auditory stimuli on a multi-media computer screen, so that the individual's responses can be monitored in conjunction with physiological responses received by biofeedback sensors. The computer tallies the test subject's recorded responses. Virtual work environments are optionally displayed, to enable the tested individual to simulate a real work environment. Unlike other job evaluation systems, the system evaluates a job candidate's ability to maintain task focus under pressure. It directly measures performance under pressure, rather than only inferring potential performance based upon selective input from a job candidate.

11 Claims, 24 Drawing Sheets

U.S. PATENT DOCUMENTS

| | | | |
|---|---|---|---|
| 4,810,197 A | 3/1989 | Hicks | 434/281 |
| 4,839,822 A | 6/1989 | Dormond et al. | 364/513 |
| 4,895,518 A | 1/1990 | Arnold et al. | |
| 4,931,934 A * | 6/1990 | Snyder | 434/236 |
| 5,017,142 A | 5/1991 | Bemis et al. | 434/220 |
| 5,100,329 A | 3/1992 | Deesen et al. | 434/327 |
| 5,102,341 A | 4/1992 | Koslin | 434/353 |
| 5,103,408 A * | 4/1992 | Greenberg et al. | 700/90 |
| 5,120,230 A | 6/1992 | Clark et al. | 434/307 |
| 5,173,051 A | 12/1992 | May et al. | 434/118 |
| 5,202,952 A | 4/1993 | Gillick et al. | 395/2 |
| 5,204,813 A | 4/1993 | Samph et al. | 364/419 |
| 5,211,564 A | 5/1993 | Martinez et al. | 434/323 |
| 5,226,819 A | 7/1993 | Takagaki | 434/236 |
| 5,240,419 A | 8/1993 | deGyarfas | 434/322 |
| 5,241,671 A | 8/1993 | Reed et al. | 395/600 |
| 5,261,823 A | 11/1993 | Kurokawa | 434/323 |
| 5,267,865 A | 12/1993 | Lee et al. | 434/350 |
| 5,275,569 A | 1/1994 | Watkins | 434/157 |
| 5,287,489 A | 2/1994 | Nimmo et al. | 395/500 |
| 5,302,132 A | 4/1994 | Corder | 434/156 |
| 5,318,450 A | 6/1994 | Carver | 434/336 |
| 5,326,270 A * | 7/1994 | Ostby et al. | 434/362 |
| 5,344,324 A * | 9/1994 | O'Donnell et al. | 434/258 |
| 5,344,326 A | 9/1994 | Ferris | 434/336 |
| 5,377,100 A | 12/1994 | Pope et al. | 364/410 |
| 5,379,213 A | 1/1995 | Derks | 364/411 |
| H1452 H | 6/1995 | Kennedy | 434/322 |
| 5,437,553 A | 8/1995 | Collins et al. | 434/322 |
| 5,447,166 A | 9/1995 | Gevins | 128/731 |
| 5,454,721 A | 10/1995 | Kuch | 434/127 |
| 5,456,607 A | 10/1995 | Antoniak | 434/323 |
| 5,473,744 A | 12/1995 | Allen et al. | 395/154 |
| 5,483,468 A | 1/1996 | Chen et al. | 364/551.01 |
| 5,496,175 A | 3/1996 | Oyama et al. | 434/118 |
| 5,511,982 A | 4/1996 | Pigache et al. | 434/350 |
| 5,540,589 A | 7/1996 | Waters | 434/156 |
| 5,551,880 A * | 9/1996 | Bonnstetter et al. | 434/236 |
| 5,671,409 A | 9/1997 | Fatseas et al. | 395/615 |
| 5,675,817 A | 10/1997 | Moughanni et al. | 395/753 |
| 5,676,551 A | 10/1997 | Knight et al. | 434/236 |
| 5,696,981 A | 12/1997 | Shovers | 395/760 |
| 5,711,671 A | 1/1998 | Geeslin et al. | 434/236 |
| 5,717,865 A * | 2/1998 | Stratmann | 705/10 |
| 5,828,943 A | 10/1998 | Brown | 434/258 |
| 5,882,203 A | 3/1999 | Correa et al. | 434/236 |
| 5,888,074 A * | 3/1999 | Staplin et al. | 434/258 |
| 5,911,581 A * | 6/1999 | Reynolds et al. | 434/236 |
| 6,029,043 A * | 2/2000 | Ho et al. | 434/350 |
| 6,067,468 A | 5/2000 | Korenman et al. | 600/547 |
| 6,149,586 A * | 11/2000 | Elkind | 600/300 |
| 6,227,862 B1 * | 5/2001 | Harkness | 434/65 |
| 6,260,022 B1 * | 7/2001 | Brown | 705/2 |
| 6,322,368 B1 | 11/2001 | Young et al. | 434/236 |
| 6,341,267 B1 * | 1/2002 | Taub | 705/11 |
| 6,615,182 B1 * | 9/2003 | Powers et al. | 705/7 |
| 6,632,174 B1 | 10/2003 | Breznitz | 600/300 |
| 6,652,283 B1 * | 11/2003 | Van Schaack et al. | 434/236 |
| 6,877,989 B2 * | 4/2005 | Embretson | 434/236 |
| 2001/0042004 A1 * | 11/2001 | Taub | 705/11 |
| 2003/0033145 A1 * | 2/2003 | Petrushin | 704/236 |
| 2003/0036683 A1 * | 2/2003 | Kehr et al. | 600/300 |
| 2003/0059750 A1 * | 3/2003 | Bindler et al. | 434/236 |
| 2003/0077556 A1 * | 4/2003 | French et al. | 434/258 |

FOREIGN PATENT DOCUMENTS

| | | |
|---|---|---|
| WO | PCT/US02/08613 | 10/2003 |

* cited by examiner

FIG. 1

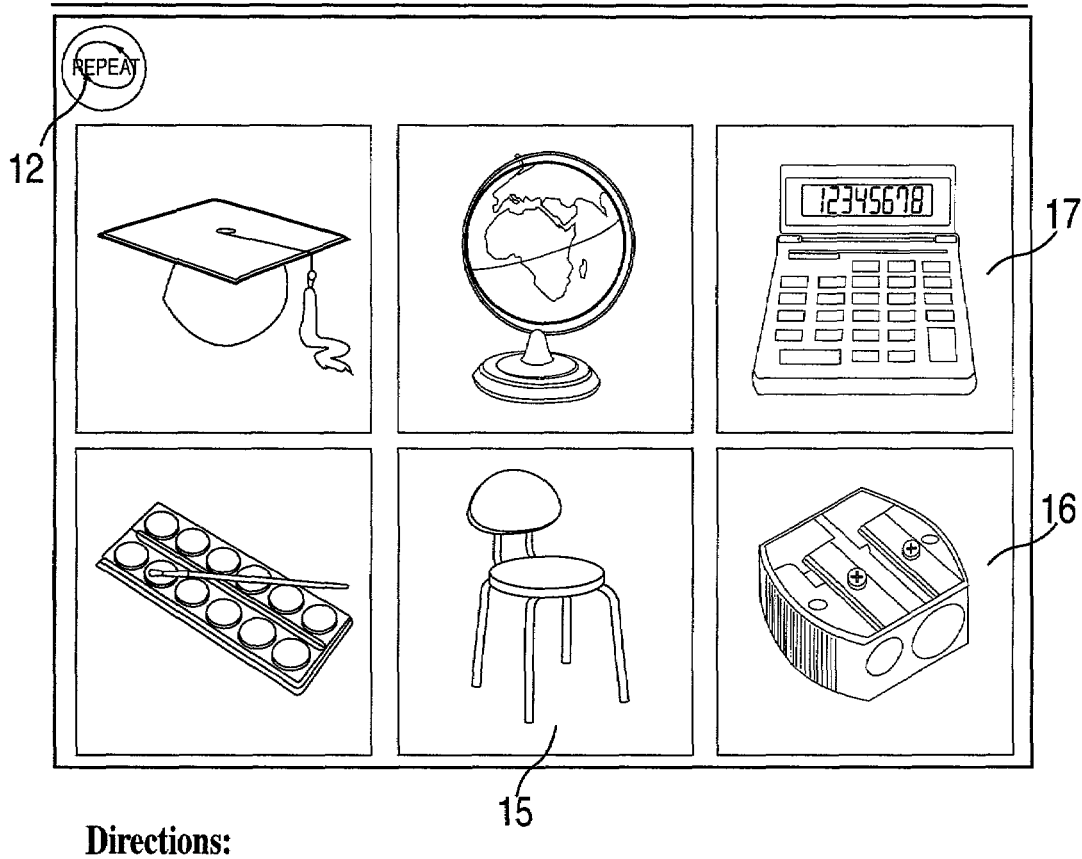

Directions:

*You are going to see some pictures. Then, you will hear a word. Click on the picture that goes with the word. You may use the same picture as your answer more than once. Let's try one together.*

Trial item 1: Chair.
*Good! Now, try some more.*
*(That's not quite right. This is the picture that goes with the chair. Now, try more)*

Trial item 2: Sharpener.
*Good! Now, try some more.*
*(That's not quite right. This is the correct answer. Now try more)*

Trial item 3: Calculator.
*Good! Now, try some more.*
*(That's not quite right. This is the correct answer.)*

FIG. 2

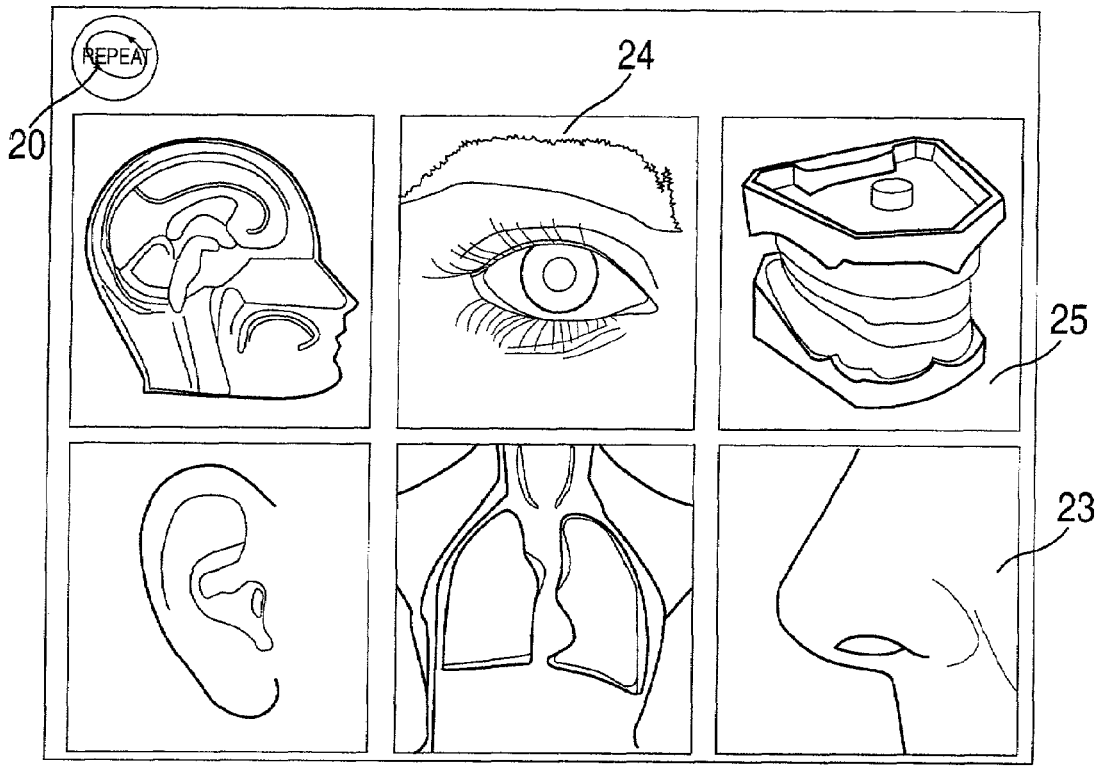

Directions:

21 { *You are going to hear some questions. Click on the picture that best answers each question. You may use the same picture as your answer more than once. Let's try one together.*

22 {
Trial item 1: Which one of these is a picture of a nose?
*Good. Now try some more.*
*(That's not exactly right. Listen again. This is the picture of a nose. Now try some more.)*

Trial item 2: Point to the picture of an eye.
*Good. Now try some more.*
*(That's not quite right. Listen again. This is the correct answer. Now try more.)*

Trial item 3: Which of these is a picture of teeth?
*Good. Now try some more.*
*(That's not quite right. Listen again. This is the correct answer. Now try more.)*

FIG. 3

Categorization

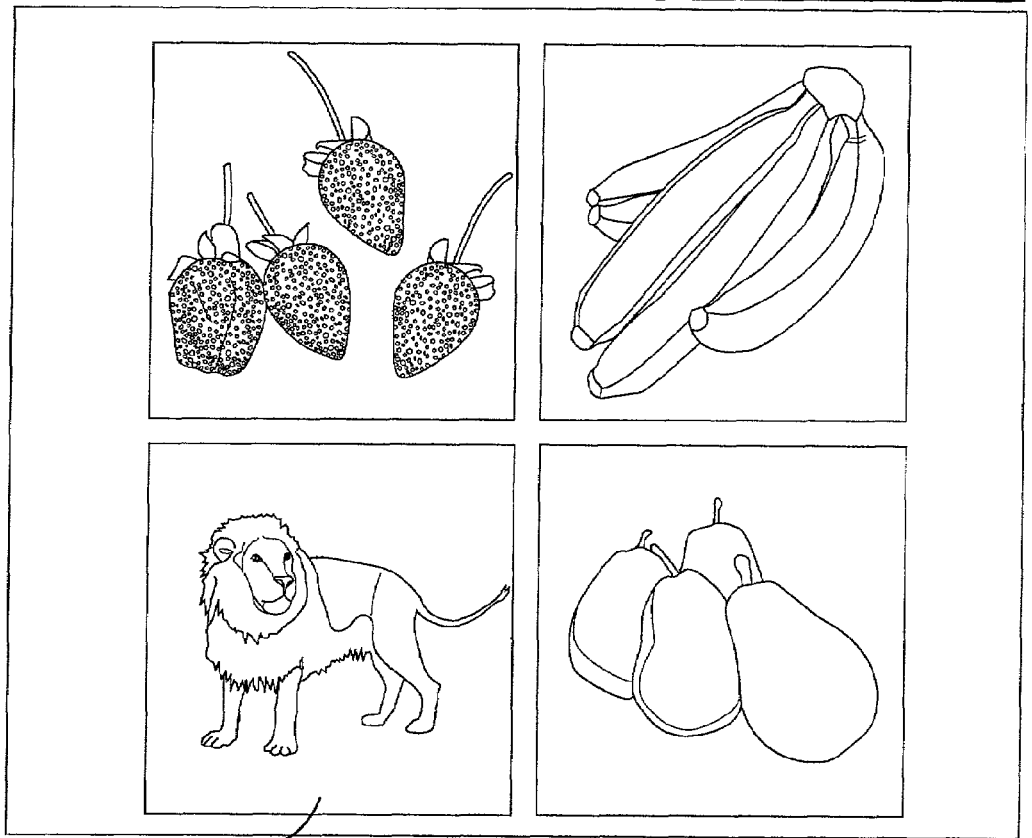

Directions:

27 { *You are going to see four pictures. Three of the pictures are alike in some way and one picture is not like the others. Choose the picture that does not belong with the others. Let's try one together.*

28 {
Trial item 1:
*Good. Now try some more.*
*(That's not quite right. These three are alike because they are all fruits. This one is not a fruit so it does not belong with the others. Now try more.)*

Trial item 2:
*Good. Now, try some more.*
*(That's not quite right. This is the correct answer. Now try more.)*

FIG. 4

Directions:

33 { *You are going to see pictures of people who are thinking or feeling many different things. Then you will hear someone speak. Choose the person that goes with what you heard. You may use the same picture as your answer more than once. Let's try one together.*

34 { Trial item 1: I don't care what you think!
*Who do you think said that?*
*Good! Now try some more. Work as quickly and as carefully as you can.*
(That's not quite right. Listen again. The boy who is speaking sounds angry. This picture is the right answer because it shows a boy that is angry. Now try more.)

FIG. 5

Auditory Memory

38 { Directions:
Before we begin, let's take a moment to review some numbers. When you hear a number, point to it on the screen.

39 {
Point to 6
Good!
(This is the number 6, try again.)

Point to 9
(This is the number 9, try again.)

Point to 5
(This is the number 5, try again.)

Point to 2
Good! Let's continue.
(This is the number 2, try again.)
Good! Let's continue.
(That's not quite right. Now, ask the person helping you to choose one of these options.)

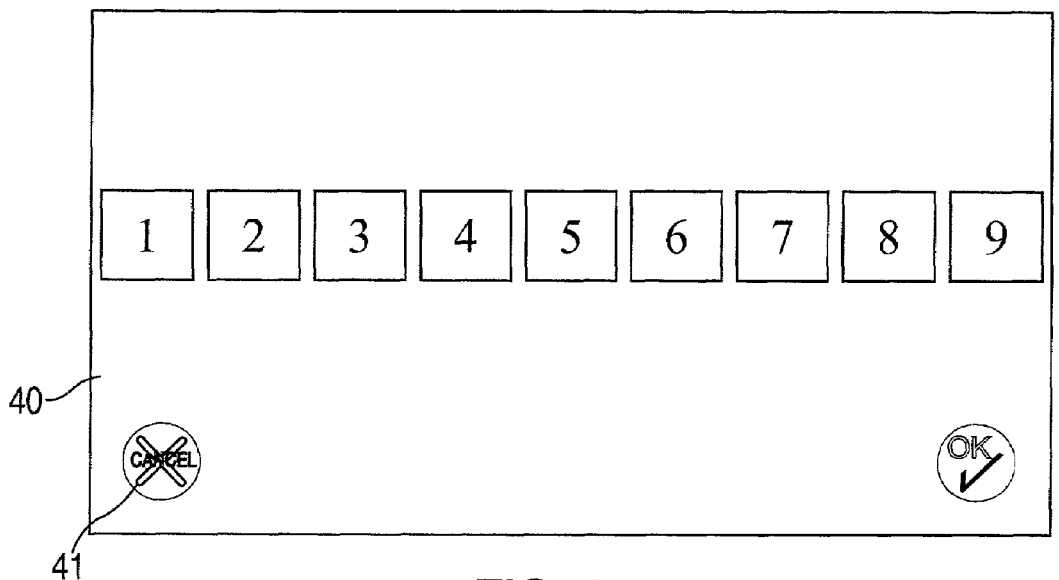

FIG. 6

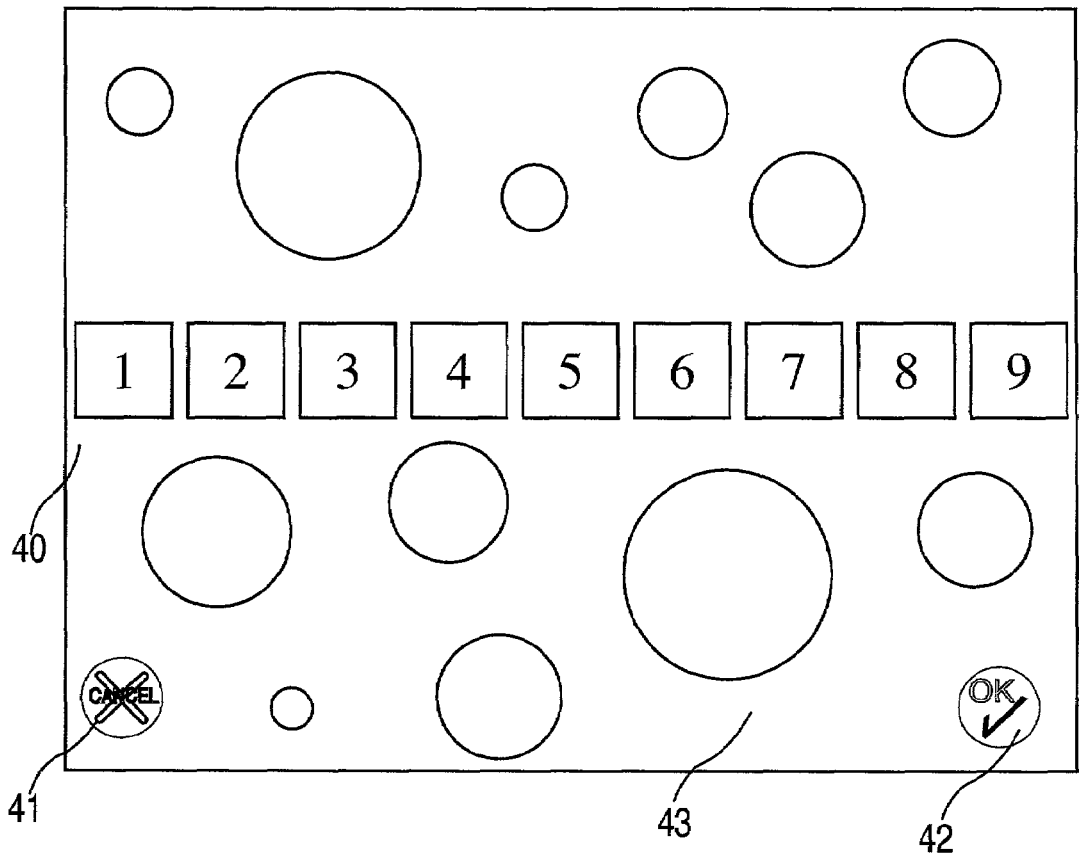

Directions:

45 { *Listen carefully. You are going to hear numbers in a certain order. Pay close attention. This time, you will see things on the screen as you hear the numbers. Click on the numbers in the same order they were said. Let's begin.*

46 { Oral administration of Auditory Memory with Visual Distractions:
*Listen carefully. You are going to hear numbers in a certain order. Pay close attention. This time, you will see things on the screen as you hear the numbers. Repeat the numbers in the same order they were said. Let's begin.*

Items:

Visual Memory

Directions:

50 { *Before we begin, let's get familiar with some new shapes. Each time you see a shape here... find it on the bottom.*

51 {
*(Shapes are presented individually.)*
*(That's not quite right. This is the right shape. Let's try it again)*

*Good! Now you are ready to begin.*
*(Now, ask the person helping you to choose one of these options.)*

*Watch the screen carefully. Shapes will be appearing in a certain order. Pay close attention. When it is your turn, click on these shapes in the same order. Click on the OK button when you are done. If you want to change your answer, you will have one chance to click on the CANCEL button... and begin your answer again. Let's try one together.*

FIG. 8

54 { Trial item 1:
*Good! Now try some more.*
*(That's not quite right. Watch how I do it. Now try some by yourself.)*

Visual Closure

Directions:

60 { *Look at the screen. A picture is coming. When you know what the picture is, click on the screen. Here it comes.*

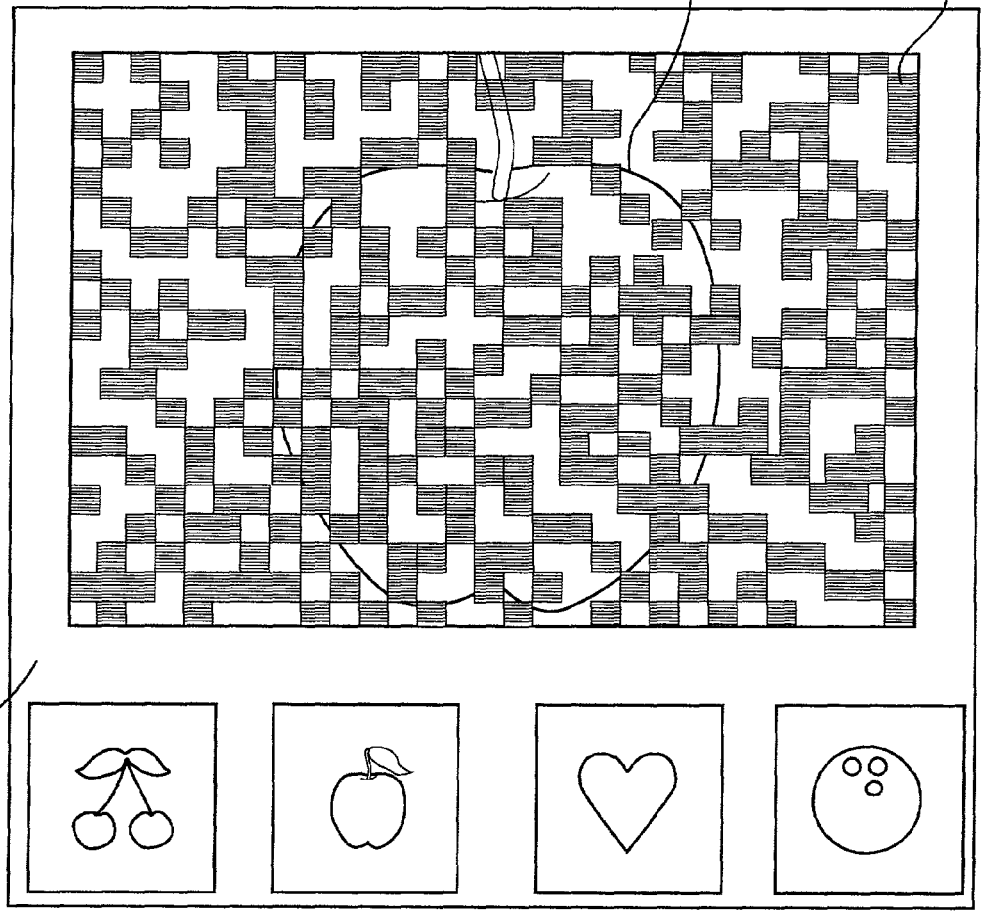

61 {
- *Please Note: The picture is revealed progressively and when the examinee guesses he clicks in the screen, the picture disappears and he gets the four symbols to choose from.*
-

*Trial item 1 (apple)*
*(Remember - click on the screen when you know what the picture is)*
*Now choose from these buttons to show what the picture is.*
*Good! Now watch the screen to see the whole picture.*
*You were right! It is a picture of an apple. Now try some more.*
*(That's not quite right. Watch the screen to see the whole picture.*
*You see, it is a picture of an apple. This is the correct answer. Now try more)*

FIG. 10

Stress:
Regular part instructions:
(BOB_1)
Look at the picture on top.

(BOB_2)
Now look at these pictures, some of them are exactly the same as the one on top, others are different.
You will be asked to choose all the pictures that are the same as the one on top.
If you make a mistake, you can change your answer by clicking on it a second time.
Watch how this is done.

(BOB_3)
This picture is not the same as the one on top.
Cancel this choice by clicking on it again.

(BOB_4)
Good.
Now find all the pictures that match the one on top.

(BOB_5)
Click on the OK button when you are done.

(BOB_6)
Now try some more by yourself.

(BOB_7)
That's not quite right.

(BOB_8)
These are the correct answers.
Now try some more.

(FINAL B 3)
You have exactly 2 and a half minutes.
You are not working fast enough, try harder.
You better work faster if you want to finish in time.
You have less than two minutes left.

FIG. 12A

You've lost some points, be more careful.
You're not working fast enough, try harder
You have a minute and a half left.
You've lost some points, be more careful.
You better work faster, if you want to finish in time.
You have only one minute left,
Hurry, you are running out of time.
You've lost some points, be more careful.
You're not working fast enough, try harder.
You have only 30 seconds left.
Hurry, you're running out of time.
You have only 20 seconds left.
You have 15 seconds to finish, 14, 13, 12, 11, 10, 9, 8, 7, 6, 5, 4, 3, 2, 1.

(GOOD)
Good, now try some more.
Remember, work as quickly and as carefully as you can.

(THIS IS)
These are the correct answers.

(TRY MORE)
Now, try more.

(WRONG)
That's not quite right.

Stress part instructions:
    "Now, Let's try some more. This time you will have only 20 seconds for each item.
        Work quickly and carefully, you will have only 2 and a half minutes to finish all of them. Be careful you will lose points for every wrong answer, ready GO."
"Congratulations! You have completed the stress tolerance test."

Name:
ID Number 12222                D.O.B.                Test Date: 1/30/2001

Please fill in the following information:

| | Baseline | After Part I (Pure Task) | After Part II (Task w/stress) | After Part III (Relaxation) | Peak |
|---|---|---|---|---|---|
| Heart Rate | | | | | |
| GSR (Galvanic Skin Response) | | | | | |
| Skin Temperature | | | | | |
| Thoracic Respiration | | | | | |
| Abdominal Respiration | | | | | |
| BVR (Blood Volume Pulse) | | | | | |
| EMG (Muscle Tension) | | | | | |
| Blood Pressure | | | | | |

PRINT

32. Drug use is a private affair.
    1. True
    2. False
33. A shoplifter should be arrested.
    1. Only if the amount stolen is more than $300
    2. Only if the amount stolen is more than $200
    3. Only if the amount stolen is more than $100
    4. Only if the amount stolen is more than $50
    5. Only if the amount stolen is more than $10
    6. In any case, no matter what amount was stolen
34. Do people cheat for personal gain?
    1. Yes
    2. No
35. How many times in the past did you witness a bribery?
    1. More than five times
    2. Five times
    3. Four times
    4. Three times
    5. Twice
    6. Never
    7. Only once
    8. Don't remember
36. Do you think drug use increases your ability to function?
    1. Yes
    2. No
    3. Depends what drug.
37. If you're already stealing, you might as well steal a lot?
    1. True
    2. False
38. Would you report minor shoplifting?
    1. Yes
    2. No
    3. Don't know
39. "People will hide their past in order to get a new job."
    1. True
    2. False
40. Is theft more severe than bribery?
    1. Yes
    2. No
    3. Don't know

FIG. 14

APPLICATION OF MULTI-MEDIA TECHNOLOGY TO COMPUTER ADMINISTERED VOCATIONAL PERSONNEL ASSESSMENT

RELATED APPLICATIONS

This application is based upon my U.S. provisional patent application No. 60/277,140 filed Mar. 19, 2001.

This application is a continuation-in-part of my application Ser. No. 09/395,548, filed Sep. 11, 1999, now U.S. Pat. No. 6,491,525 B1, which is a continuation of application Ser. No. 08/829,488, filed Mar. 27, 1997, now U.S. Pat. No. 6,030,226 dated Feb. 29, 2000, which is based on Provisional Application Ser. No. 60/014,203, filed on Mar. 27, 1996.

FIELD OF THE INVENTION

This invention is related to interactive multi-media applications in psychological testing for vocational assessment, which evaluates a job candidate's ability to maintain task focus under pressure, rather than only inferring performance based upon selective input from a candidate.

INCORPORATION BY REFERENCE

My above noted prior applications are incorporated by reference herein. My prior patent applications are concerned with applications of multimedia technology for psychological and educational assessment tools. My prior applications are an improvement over conventional psychological and educational assessment tools which have been used for the measurement and evaluation of abilities, aptitudes, personality characteristics and so forth, such as the intelligence quota (IQ) test dating back to 1904 of the French psychologist Alfred Binet that would identify slow learners.

The specification and drawings of my patent points out the basic difference between the application of multimedia tools to psychological and educational assessments that are the subject of my invention and, in contrast, the rudimentary skill acquisition or remedial training tools commonly known as computer-assisted instruction (CAI). In computer assisted instruction (CAI), courseware is provided for teaching presentations in various learning areas. Unlike my prior invention, in computer assisted instruction (CAI), the subjective factors of reliability, validity, bias, and standardization are seldom of central importance because of the objective teaching nature of the CAI courseware.

In contrast, my patent discloses that these subjective factors are of primary importance in the psychological and educational assessment tools, and that accurate determination of the tested subject's basals and ceilings is required for the proper administration and scoring of the psychological assessment test, which is used in education. My patent also points out that video and audio presentations are mainly matters of variable style or perceived effectiveness in the computer assisted instruction (CAI) environment.

Further in contrast, with respect to psychological assessment, assessment tools are rigorously field tested (i.e. "normed") for reliability and validity, and their mode of administration is precisely stipulated, and any deviation may violate the conditions under which it had been normed.

My patent points out that psychological and educational assessment tools can utilize the full range of multi-media presentation features which closely simulates the manual version of a normed test. In my patented application of multimedia technology, the standards used to create the manual test are easily translated to the computer test by a comparative study of the similarity of test scores of computer assisted versus manual testing.

My patent also emphasizes that Computer Assisted Instruction (CAI) is used to teach new material, to review learned material as in drill and practice, to teach productivity techniques such as word processing and to teach programming, and to keep track of scores or to adjust the level of difficulty.

In contrast, the Computer Assisted Assessment (CAA) of my invention is an assessment tool, so that teaching is not the objective. Scoring of Computer Assisted Assessment (CAA) is sophisticated with raw scores, standard scores, sub-tests, age equivalents, and basals and ceilings. The testing rules of Computer Assisted Assessment (CAA) are rigid with no deviation allowed.

My prior patent emphasizes that a clinical psychological tester can use the Computer Assisted Assessment (CAA) with its attendant multimedia tools, in the area of question sequencing and scoring related to establishing the critical range of the tested subject, and that the subject's basals and ceilings are determined by runs of right or wrong answers within a particular sequence. My patent also discusses a method for reducing bias, such as social class prejudice or the assumption that shy or disruptive children are learning impaired.

My patent also overcomes that fact that some clinicians may be very proficient in their respective fields, but that they may not speak clearly, which causes confusion. My patent reduces the probability that a tested subject will get a question wrong just because he or she doesn't understand the examiner, especially in English as a Second Language (ESL) subjects.

My patent also overcomes the limitations of standard Computer software for test scoring and analysis of error patterns, which is available for manually administered tests. But these computer-assisted tests are not constantly re-evaluated, and the computer provides no computer guidance in administrating the test, since this is done as an ad-hoc procedure after the test is over.

In the "Summary of the Invention" portion of my patent, there is described a method and system to perform psychological and educational assessment of subjects using multi-media technology.

The method described in my patent is for psychological and educational evaluation of human subjects, which includes the steps of providing a human subject, such as a student, to be evaluated, with a multi-media capable computer having a view monitor means, such as a VDT terminal, and a computer input-response means, such as a keyboard, a mouse or a touch screen. In that patent, it is noted that a human psychological tester optionally operates the multi-media computer and conducts the psychological evaluation of the student.

My patent also discusses the option that the multi-media computer has a linguistic adaptation means, such as a sound card and data associated therewith, which can produce sounds, such as test instructions, in the most appropriate language and dialect of the test taker, such as a student, so that the human tester can provide the human subject with instructions for responding to the psychological evaluation.

As for multi-media technology, my patent discusses that a human subject being psychologically evaluated is exposed to computer-generated multi-media psychological evaluative probing, so that the human subject can respond to the computer-generated psychological evaluative probing.

This feature is reiterated in my new patent application for my present invention in the field of psychological evaluation of subjects during psychological vocational assessment. In both my patent and the present invention herein, the computer tallies and records the subject's responses and analyzes the human subject's recorded responses. Afterward the computer automatically prepares a report based upon the human subject's recorded responses, and transfers its report, such as by transfer to a computer-readable diskette or by printing to a printer.

In both my earlier patent and in my present invention for vocational assessment, the psychological evaluation of the human subject is provided by at least one software program stored in a randomly accessible non-volatile computer memory, such as the computer's hard drive, for providing at least one type of psychological evaluation. The at least one software program further includes a plurality of discrete audible and/or visual segments such as questions to be responded to by the human subject being evaluated.

The discrete audible segments include audibly reproducible signals stored in a randomly accessible non-volatile computer memory for producing sounds to be responded to by the human subject being evaluated, such as spoken phrases to be responded to by the human subject. The spoken phrases are selected from a plurality of user-selectable languages and/or dialects.

The discrete visual segments include visually-reproducible signals stored in a randomly accessible non-volatile computer memory for producing images to be responded to by the human subject being evaluated, such as text selected from a plurality of psychological evaluation question items stored as text written in a plurality of languages and/or dialects and/or character sets, such as Chinese or Cyrillic, among others.

My patent also discusses the fact that to assist in evaluating temporal time oriented tasks, such as allowing a person decide which of a plurality of moving objects, such as balls, moves fastest, or the calculated destination thereof, optionally the discrete visual segments may include computer-generated motion for psycho-motor evaluation of human subjects.

My patent discusses that computer-generated motion may include a plurality of user selectable visually perceived motions, such as the moving balls, at differing speeds and/or velocities and/or accelerations.

Moreover, my patent also discusses that the software program can present audible psychological probing tasks in a variety of user-selected languages and dialects, wherein the languages and dialects are respectively stored discretely in randomly accessible computer non-volatile memory, such as the computer's hard drive or upon a removable diskette.

In both my patent and in my present invention for vocational assessment, the method of using multi-media technology in psychological evaluations may include an evaluation of the human subject's emotional status, mental health, learning ability, neurological impairment status, educational status, educational achievement status, aptitude for future education or aptitude for future vocational education.

In the "Brief Description of the Drawings" portion of my patent, there was disclosed multi-media equipment which is used in a test session for psychological evaluation.

My patent disclosed typical video display screen's views of various multi-picture panels used in the computer assisted psychological assessment.

My drawings also disclosed video displays using screen panels, optional animation and voice response modes.

The drawings of my patent also show a video display screen sequence of the multi-media system with clarifying instructions and "Dynamic Linguistic Adaptation" portions.

My patent also shows various exemplary video display screens that illustrate modeling proper response sequences for sample questions.

My patent also provides for an input response means 23 which is used to input communicated sensory data from the human subject to multi-media computer to conduct a psychological evaluation of the human subject.

My patent also discloses how a computer-responsive user selectable means, such as a keyboard, allows a psychological tester to select pre-recorded test instructions in appropriate languages and dialects appropriate to the language and dialect of human subject being tested.

My patent also uses the multi-media tool of an audible playback which audibly communicates one or more sets of pre-recorded test instructions, with audible playbacks having sound cards and data associated therewith, to produce audible test instruction sounds, in the appropriate language and dialect thereof.

My patent also discloses a multi-media software program that includes a plurality of discrete audible and/or visual segments such as questions to be responded to by the human subject being evaluated. In my patent, a user-selectable set of computer-generated multi-media psychological evaluative probing data communicates with the audible playback, and a recorder records responses of the human subject in response to the computer-generated psychological evaluative probing. The human subject's responses are tallied.

In my patent, a computer output printer automatically prepares a written record of the human subject's recorded responses in a written report, which report is transferred to a computer, and is stored in the randomly accessible non-volatile computer memory of the multi-media computer.

My patent also shows a psychological assessment session, using a multi-media system to give the same type of test as is done in conventional human-to-human evaluations. My patent discloses how a tested human subject sits facing a computer screen on a video display terminal of a multi-media personal computer, wherein the subject uses pointing device to indicate his or her answers.

My patent also discusses various multi-media computer components, such as a mother board containing a microprocessor and other modules and support electronics, with optional extra random access memory (RAM), a hard drive, a floppy drive using removable media (diskettes), a CD-ROM with a removable compact disk (CD), a sound board and a variety of sockets or ports to support a speaker, a microphone, a display, a mouse port and a keyboard socket.

My patent gives a non-limiting example of an appropriate multi-media computer, such as a Packard Bell model AX3510, which has 8 MB RAM, a 1000 MB hard drive, Quad speed CD-ROM, stereo speakers and an Intel 100 MHZ Pentium processor.

My patent explains that Computer Assisted Assessment tools may run on a 33 MHZ '386 class processor with a 100 MB hard drive, single speed CD-ROM and 4 MB of RAM, or a notebook computer having similar capability with integral liquid crystal display (LCD).

My patent discloses that any type of pointing device can be used; such as, for example, a mouse, track ball, video game control, joy stick, or even a finger when used with a "touch screen", as well as other display technologies such as plasma displays or Texas Instrument's micro-mirrors, which can support 3-D presentation displays, which are most appropriate in psychological assessment tests.

My patent shows that educational and psychological assessment test content is prepared using state-of-the-art multi-media authoring tools combining audio, picture and text sources, which improves over the manual administration of these psychological assessment tools, so that the automatic nature of using a computer precludes bias in test administration.

My patent reiterates that computer administration enhances on-task performance of the person being tested, in a non-biased fashion, so that test standardization is assured by computer administration.

My patent shows that multi-media technology can selectively first show an image with a plurality of objects, and then can eliminate a number of the presented objects to focus the tested subject on an appropriate response.

My patent also shows that animation can be used in creating new measures dealing with temporal issues, such as movement of objects, which is also appropriate in my present invention which, among other features, can virtually simulate a vocational environment of a job candidate. My present invention also shows that animation can also test cognitive skills in predicting events related to the virtual work environment. In my present invention, a multi-media computer is ideally suited for assessment tools that require the use of timing, to replace assessment evaluations requiring the use of a stopwatch by the clinician to either time the presentation of materials or the period for timed responses (or both).

My patent also shows that a multi-media computer may have voice recognition software of proper quality that it can reliably recognize the utterances of a tested subject and that a microphone can be used to field the responses and determine if an answer is right or wrong, or if more than one response has been given.

Such state-of-the-art of voice recognition software is disclosed in software of Syracuse Language Centers, which run on a 386-class computer with 4 MB of RAM and are capable of analyzing the pronunciation of words automatically.

My patent also discloses that different keys on a keyboard or pointer can also be linked to specific verbal responses or prompts. For example, if the test subject gives an ambiguous answer, the computer can audibly say, "Explain what you mean." In the present invention, the computer can evaluate stressful assessment situations, by uttering critical statements, such as, "You're not working fast enough," and then can use biofeedback monitoring to evaluate the subject under stress.

My patent discusses the use of appropriate language dialects, as well as an "assisted voice recognition" system which uses a keyboard and no microphone. In this system, keys on the keyboard are mapped onto special functions by the testing software, wherein responses of a tested subject may be responded to with an audio feedback such as, "Please respond with only one answer" every time one of the "Invalid" keys is pushed.

My patent also discusses how incorrect answers can be responded to if answered incorrectly. The test can be automatically terminated if the test subject never gets beyond an initial stage. After the test, a raw score is updated, the basal/ceiling analysis is performed, the test score is updated, the sequence is changed if necessary, and the subsequent following question is presented (or the test is ended). This general flow can be used with pointing as well as verbal answers. It is understood that other logical flows can be used to achieve an equivalent result without deviating from the scope of this invention.

My patent also demonstrates various video display screens displaying multi-media techniques in modeling appropriate responses for sample questions. The drawing Figures show screens with pictures of objects wherein the tested subject is asked to point to one of the objects and if the answer is incorrect, the respective display screen shows the image corresponding to the correct answer. By not showing the other two images in the same screen in the present invention, the student's attention is focused on the correct answer.

My patent also shows a typical example known as a CREVT-CA program, which shows how the method and system of the present invention is used in one illustrative example. In this example, a sample psychological/educational assessment test is run in a computer program designated as the "Comprehensive Responsive and Expressive Vocabulary Test-Computer Administered" (CREVT-CA).

To start the CREVT-CA program, the user double clicks on the CREVT-CA icon in the CREVT-CA Program Group. If the user has installed the program in WINDOWS 95®, from the start menu, the user selects "Programs, CREVT Program Group", with the CREVT-CA icon. After the opening title, the Main Menu appears. Six choices on this screen are available to the user, such as:

(OK) Administer Tests
(OK) Score Expressive Subtest
(OK) View a Previous Record
(OK) Change the Password
(OK) Recharging Information
(OK) Exit To choose an option, the user points and clicks on the box next to the operation the user wishes to bring forth.

My patent also shows how a typical program, such as a CREVT-CA is used to administer a test to an individual.

In the CREVT-CA example, the user can choose to administer both the Receptive and Expressive sub-tests or individual sub-tests.

Then, user the completes the demographic information screen.

The user selects an appropriate language and dialect of the test subject, such as a child, such as "French-Quebecois" vs. "French-Haitian Creole", or "English-Australian" vs. "English-Southern American" and the like. When this is done, the user clicks on the "OK" button to continue.

Finally, the user chooses which form of the test the user would like to administer—Form A or Form B. If the user is administering both sub-tests, the form selection applies to both sub-tests.

Whether the user has chosen to administer the Receptive Vocabulary Subtest, or both Sub-tests, the testing begins with the Receptive subtest. The subject is seated in front of the computer with the mouse in hand (in other test environments, the examiner may input information from the subject, who is tested in a hands-free environment). During the Receptive portion of the test, a voice in a pre-selected language and dialect pronounces a word while the subject views the pictures. In this example, the subject simply uses a pointer, such as a computer mouse to point and click on a picture to indicate an answer.

As soon as a ceiling is reached (when the subject misses two consecutive items in the set of items) the program automatically moves on to the next set of pictures.

If the user is using the CREVT-CA program to administer the Receptive portion of the test but is administering the Expressive portion without the computer's assistance, the user can still have the CREVT-CA compute the standard scores, percentiles, and age equivalents for both sub-tests together. When the Expressive and Receptive sub-tests are completed, and after the user has finished the Receptive test on the computer, the user simply clicks on the "yes" button to choose to score the Expressive subtest as well. The CREVT-CA program asks the user to enter the raw score of the Expressive subtest and then computes the Receptive, Expressive, and Composite scores.

After the Receptive subtest is completed, the user needs to enter the user's password to be able to view the scores (the password is initially set to "CREVT"). First, the screen displays a graph of the percentage of correct answers per set of pictures. This graph can be printed by clicking on the "OK" button next to the word "Print" at the bottom of the screen. To continue on and to view the subject's scores, the user clicks on the "OK" button next to the words "Continue" and "View Test Scores".

The Expressive portion of the test is given on the computer after the Receptive portion or by itself. The computer gives the instructions orally and asks the subject to define a series of words.

The Expressive Subtest automatically ends when either a ceiling is reached (i.e., when the subject misses three consecutive items) or when the last (25th) item is administered.

According to my patent, when the testing is finished for a particular subject, the examiner enters a password (the password is initially set to "CREVT") to view a comprehensive report of the test results on the computer screen. The examiner can then print out a hard copy of the report by clicking on the "PRINT" button at the bottom of the scores screen. If the Expressive subtest was administered and some information was saved in the "SUBJECT'S REPLY" text boxes, the examiner has the option of also printing out those replies.

The CREVT-CA program also allows the user to graph the standard scores obtained by the subject, along with up to seven standard scores with means of 100 and standard deviations of 15 obtained when using other tests with the subject. To print, the user clicks on the "OK" button next to the work "PRINT" on the bottom of screen displaying the graph.

To view the scores of a subject who took the test previously, the user chooses to view a previous record option from the Main Menu. The user enters the name of the subject whose record the user wants to see. The user can search for a record by last name only or by first and last names. The user can also choose to view the database record by record. Once the desired record is displayed on the screen, the user can choose to view either the subject's scores or the subject's responses to the Expressive Vocabulary subtest. The user can also print out hard copies of either of these items.

In my present invention, it is noted that many of the aforesaid multi-media applications can be specifically used in the field of vocational psychological assessment, to ascertain whether a tested subject is suitably fitted for a particular job. Not only can the person's cognitive aptitude be determined, but the tested person can be monitored while subjected to non-stressful and stressful situations, to simulate the rigors of a particular job or the person's suitability in general for a particular job.

BACKGROUND OF THE INVENTION

Various attempts have been made to use computers in vocational assessment. For example, U.S. Pat. No. 5,326,270 of Ostby discloses use of a computer for pre-employment screening, but it is more of a role playing game that is also applicable to training. The emphasis on "path analysis" in assessing task-processing style has no counterpart in the present invention.

U.S. Pat. No. 4,627,818 of Von Fellenberg discloses a very exacting method for presentation of paired questions and analysis of their results for identifying subject's psychological traits.

U.S. Pat. No. 4,683,891 of Cornellier discloses a computerized employment training using biofeedback monitoring to enable a subject to increase his tolerance of stress and enable him to perform tasks under more stressful conditions, using goal oriented cognitive tasks.

U.S. Pat. No. 5,551,880 of Bonnstetter discloses an Employee Success Prediction System, using a computer to administer testing, but appears not to use graphics or multimedia. The testing in Bonnstetter '880 uses questionnaires. Both behavioral and value profiles of a subject are obtained.

In addition, it has been found previously in the prior art, primarily from testing for integrity on polygraph tests, that questions that take longer to answer and that exhibit more response time latency variability are not being answered truthfully.

However, these prior art patents and polygraph integrity testing do not disclose a multi-media method and system which performs psychological assessment of an individual for suitability for particular jobs, whereby the individual is shown and provided with discrete visual and auditory stimuli on a multi-media computer screen, so that the individual's responses can be monitored in conjunction with physiological responses received by biofeedback sensors.

These prior art patents and integrity testing also do not disclose display of virtual work environments, to enable the tested individual to simulate a real work environment, so that a job candidate's ability to maintain task focus under pressure can be measured, rather than only inferring potential performance based upon selective input from a job candidate.

OBJECTS OF THE INVENTION

It is therefore an object of the present invention to provide a computer administered modular multi-media normed personnel evaluation and vocational assessment system.

It is also an object to be able to evaluate test performance, interpretation and scoring criteria which evolves over time to reflect changes in the population subjected to the various test modules to establish norms more representative of the current population.

It is yet another object to provide multi-media software and tangible technology which is delivered as portable media, such as CD-ROM, diskette, DVD, computer compatible input media, or software which is downloaded and administered from the Internet.

It is also an object to provide for pre-employment screening, on the job promotion/retention/length of development screening and pre and post training evaluations which contain job performance modules as well as aptitude subtest modules.

It is also an object to provide a menu derived from subject population statistics for particular job titles, which is presented for reflecting the suitability of various test modules, the suggested weight for each module and the pass/fail limits of each module compared to subject population statistics.

It is also an object to provide a vocational assessment tool wherein the test administrator can modify the module selection, the pass/fail limits, and the weights assigned to each module for a particular job title or for a particular individual, in a variety of job performance modules.

It is also an object to provide a computer administered multi-media stress tolerance test that compares a subject's performance on a visual matching task under two conditions, non-stress and stress, by using test shapes which are selected to minimize ethnic bias and cultural differences.

It is further yet another object to provide a multi-media vocational assessment system which utilizes physiological sensors to actually measure and quantify changes in the autonomic nervous system of the person being tested, thereby detecting the onset of such changes and the degree of such changes during the stress test.

It is also an object to provide a vocational system which can test a subject's reaction to psychologically induced stress, with that induced by physical means, such as by a standard treadmill test sequence.

It is also an object to provide a multi-media vocational assessment, whereby images are revealed progressively, wherein the subject identifies emerging pictures and the required by the subject to make his or her identification is evaluated.

It is yet a further object to provide a computer administered integrity test module wherein questions are dispersed and repeated throughout a test, to detect deceptive answers.

It is also an object to provide a computer-generated vocational assessment test which uses virtual reality images and sounds to simulate various vocational work environments, to ascertain the best placement of a potential worker.

It is therefore also an object to provide a computer-generated vocational assessment system which uses virtual reality images to selectively reject persons who have vestibular or motor coordination problems not suited for the work environment being simulated.

It is also an object of the present invention to improve over the disadvantages of the prior art.

SUMMARY OF THE INVENTION

In keeping with these objects and others which may become apparent, the present invention provides a battery of tests which are administered to an individual by a computer using multi-media features. This normed testing can be used to assess the suitability of an applicant for employment, although other versions of the test emphasizing the stress tolerance module can also be used for screening candidates for high-stress or high-risk mission critical assignments. The primary objective of this invention is to reliably and accurately predict real world success using an easily administered rapid assessment technique.

As the performance and scoring of these normed tests evolve over time, an important feature of this assessment system is to maintain a database of field experience to continually refine the norms to insure that they are representative of the current population of individuals subjected to these tests. Updates of these norms are distributed to customers. The actual software product is delivered to customers as portable media such as CD-ROM, diskettes, DVD or similar computer input media. It is also available for download to a test administrator in secure fashion from an Internet web site. Direct use from a web site on the Internet or on a company intranet is another option for test delivery.

For example, the multi-media software may have an interface utilizing one or more computer input hardware devices such as a mouse, a keyboard, a touch pad, a microphone, a camera, physiological sensors or any other computer input device. The software is delivered to a test administrator as portable media such as CD-ROM, diskette, ROM, non-volatile RAM, flash media, DVD or other computer compatible input media.

The software may be also be downloaded from the Internet, where access is obtained through the Internet. The tests may be administered through the Internet and the related administrative functions may be performed through the Internet. When the Internet is used, there may be secured communication, wherein the secured communication is implemented with one or more security technologies, such as an internet protocol security, a secure socket layer, a private key encryption and/or a public key encryption or may utilize a VPN or other form of secure tunneling technology.

Moreover, the present invention includes a personnel evaluation system with one or more multimedia computers for sending and receiving audio and visual stimuli, each connected to respective central processing units to administer a pre-employment evaluation, a pre-promotion evaluation, a pre or post training evaluation, a personnel development/leadership training evaluation, or other form of employment evaluation application evaluation and to perform an analysis of input data. The software application stores and evaluates all input data and includes one or more modules to monitor and re-scale non-truthful responses of prospective employees, wherein one or more interfaces constantly monitor a physiological state of a subject. These interfaces induce stress inducing audio and visual stimuli and administer the evaluations with race, gender, ethnic, and cultural neutral stimuli. Optionally the interface may interact with the subject in their native language, and dialect. The interface assesses various aspects of the subject which might affect work performance, such as intelligence, interest, values, emotional status, mental health, neurological impairment, education, social apperception and aptitude of the subject being tested. The system can detect for untruthful responses and re-scale values of questions depending on the type of test and detect physiological changes in the subject. These physiological factors which are monitored by biometric sensors include measuring one or more of the following: galvanic skin responses, muscle tone, facial expressions, pupil dilation, heart rate, EKG electrocardiogram responses, blood pressure, thoracic respiration, abdominal respiration, saliva composition.

One popular use for this invention is for pre-employment screening. A menu derived from subject population statistics is presented to the test administrator by the software which displays the suitability of the various test modules, the pass/fail limits, and the weight assigned to each module, all with respect to a particular job title. The administrator can modify these suggested parameters to tailor the screening to his department needs. The job performance modules include tests for Integrity, Aptitude, Loyalty, Stress Tolerance, Memory, Social Awareness, Communications Skills, Performance Efficiency, Distractibility, and Impulsivity. Aptitude sub-tests include Visual Closure, Visual Analogies, Categorization, Information, Personality, Interests, and Values.

The computer administered multi-media stress tolerance test module compares a subject's performance on a visual matching task under two conditions, non-stress and stress. The visual matching task uses pictures of 3-D shapes and objects that are carefully selected to avoid bias to different ethnic groups or socio-economic status. Stress factors used are audio coaching telling the user to hurry, chiding the user for making errors, and short time limits for test segments. For certain applications such as screening candidates for critical missions, physiological sensors that actually measure and quantify changes in the autonomic nervous system are attached to the subject. These sensors detect the onset and degree of such changes before, during and after the stress test. Sensors on the subject's chest, arm, and fingers measure heart rate, EKG electrocardiogram responses, skin temperature, skin conductance, muscle tension, respiration rate, facial expressions, eye pupil dilation, galvanic skin responses, muscle tone, facial expressions, thoracic respiration, abdominal respiration, saliva composition and blood pressure and the changes and degree of changes, in all of the above, before, during and after the stress test. Additionally, digital recording of facial expressions and pupil dilation are made. Thus, these changes and the degree of change of these physiological parameters are monitored during the entire test module session. Combined with subject recovery time data, a very comprehensive study of the reaction to physiologically induced stress can be made in a clinical environment. Examination of difference scores for correct matches, errors of commission, and errors of omission provides a rapid and precise indication as to the degree to which an individual is affected by stress as well as the analysis of the likely type of error an individual would make under stress.

Several aptitude sub-tests using computer multi-media techniques are used. Although they are similar to namesake paper-and-pencil tests in objective, they are greatly enhanced by the capability of the computer. Professional voice actors are used to present audio instructions or test questions thus eliminating variability due to communications capabilities of "test givers".

For example, modules to test memory and distractibility is very difficult to administer in a consistent fashion in any other manner.

All of the following combinations are administered: visual memory, auditory memory, visual memory with visual distraction, visual memory with auditory distraction, auditory memory with visual distraction, and auditory memory with auditory distraction. The subject's performance is also measured on memory modules without distracters, to measure the degree of subject distractibility and to measure the specific modality of subject results, which compares performance without and with distractions, to measure the degree and type of specific modality of distraction that the subject finds most disturbing.

A computer administered multi-media visual analogies test module uses a combination of audio instruction with presentation of two 3-D color pictures of geometric shapes related in some way followed by a third picture which is related in the same way to one of five choices presented.

The shapes are chosen to minimize bias to different ethnic groups or socio-economic status. A visual closure test is efficiently administered as a picture is revealed progressively as it replaces random background elements.

The test is scored both by the accuracy with which the subject identifies the emerging picture as well as by the degree of completion (i.e. time) required by the subject to make the identification. A computer administered social apperception test presents an array of high-resolution pictures of people in a variety of postures and facial expressions. The audio presents a spoken statement. The subject is to choose the picture of the person most likely to have made that statement using visual body language and expression cues to pick up the subtle nuances of emotion depicted which reflect that of the spoken statement, as well as the nuances of expression and emotion involved.

A computer administered integrity test involves a set of written questions with multiple-choice answers. Subsets of questions with related subject matter are dispersed throughout. The answers to the related questions are analyzed as to response time latency variability to detect attempted deception.

A computer-generated and administered vocational assessment system uses virtual reality techniques to simulate a variety of vocational work environments or specific situations to ascertain the best placement of a potential employee. This is accomplished by generating specialized test modules or by substituting virtual reality images and sounds within the format of the job performance and aptitude sub-tests described above.

BRIEF DESCRIPTION OF THE DRAWINGS

The present invention can best be understood in conjunction with the drawings of my aforementioned U.S. Pat. No. 6,030,226, as well as the following drawings in which:

FIG. 1 is a test module menu for a "driver" job title of the multi-media vocational assessment system of the present invention;

FIG. 2 is a screen image and audio for a Vocabulary test thereof;

FIG. 3 is a screen image and audio for an Information test thereof;

FIG. 4 is a screen image and audio for a Categorization test thereof;

FIG. 5 is a screen image and audio for a Social Apperception test thereof;

FIG. 6 is a screen image and audio for an Auditory Memory test thereof.

FIG. 7 is a sample for a screen image and audio for an Auditory Memory with a Visual Distraction test thereof.

FIG. 8 shows audio instructions for a Visual Memory test thereof;

FIG. 10 shows a screen image and an audio for a Visual Closure test thereof;

FIG. 12A displays audio for a Stress Tolerance test thereof;

FIG. 12B displays a continuation of the audio for Stress Tolerance Test as in FIG. 12A;

FIG. 13B shows a biofeedback monitoring screen for a Stress Tolerance Test thereof;

FIG. 14 shows a screen image from a sample for an Integrity test thereof; and, FIG. 15 shows a screen image for a virtual reality depiction of a work environment.

DETAILED DESCRIPTION OF THE INVENTION

Figure 1:
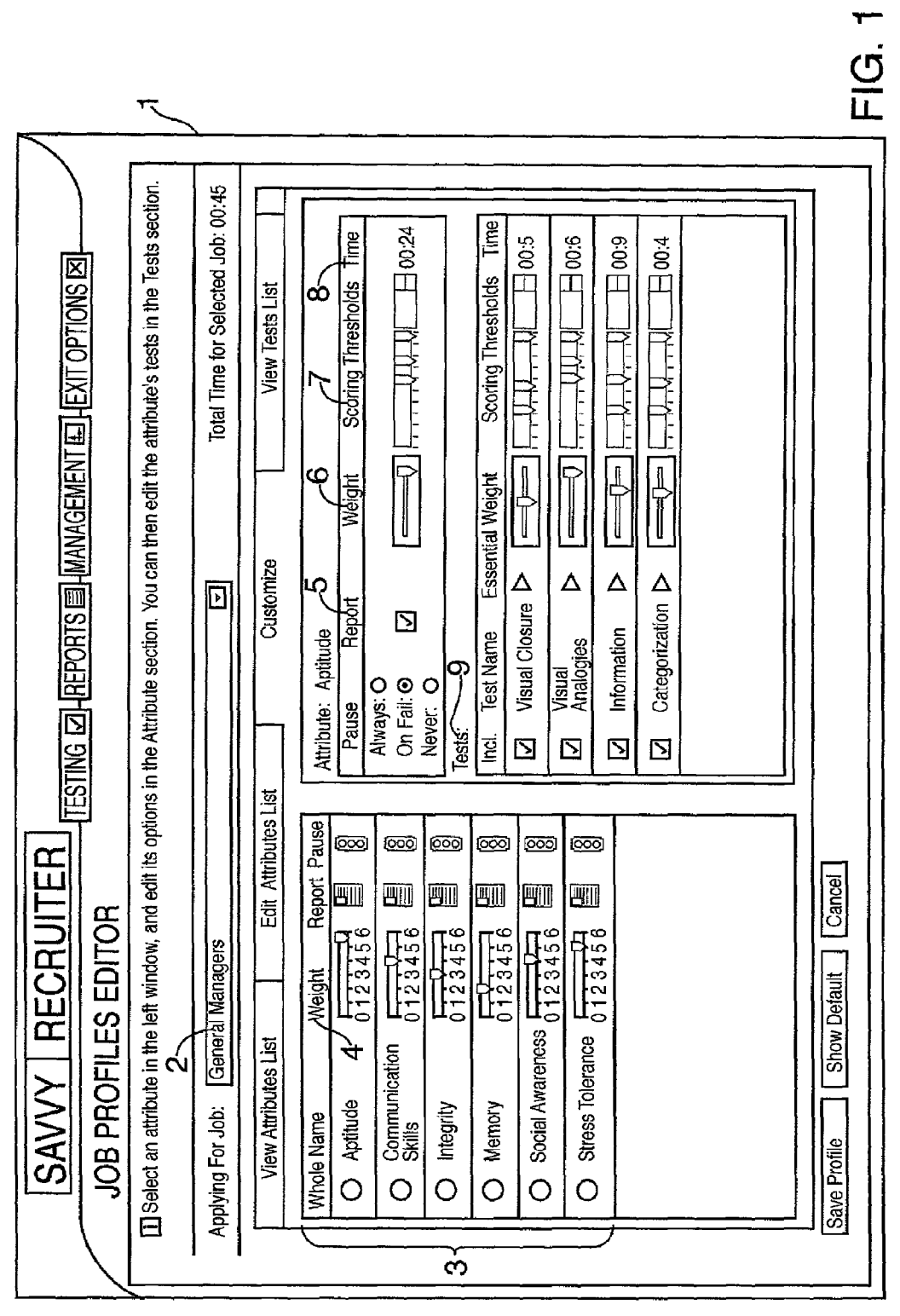
Figure 9:
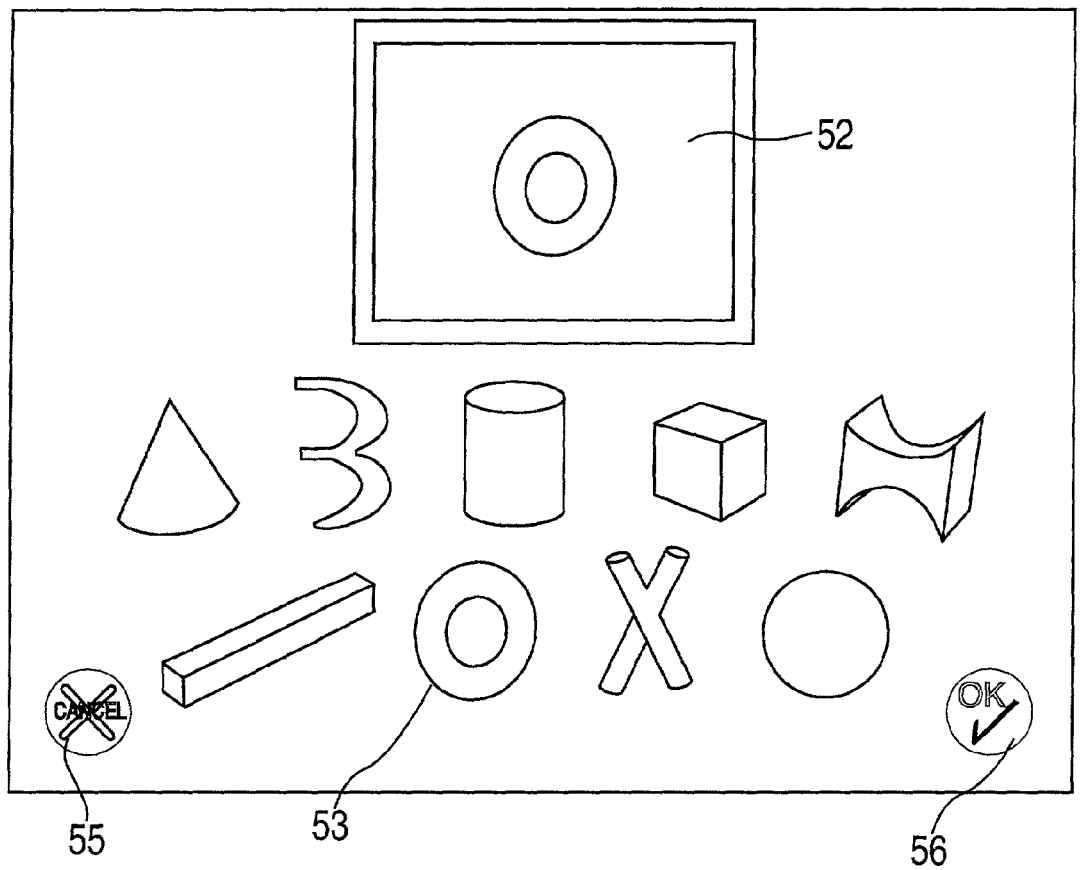
FIG. 9 shows a screen image and an audio for a Visual Memory test thereof.

When used for pre-employment screening of individuals, the testing system of this invention presents an initial menu screen 1 to the test administrator as shown in FIG. 1. The name "SAVVY RECRUITER" indicates a trade name of Applicant. Menu screen 1 is identified with a specific job title 2, which is a "general manager" for this example. The job attributes 3 are presented in a column format to the left and their applicability to this specific job title 2 is presented in "weight" 4 column to the immediate right. A job attribute 3 such as "Aptitude" is weighted as being more relevant than "Memory" for the job title 2 of general manager.

For a specific job attribute 3, such as "Aptitude", a report may be generated by clicking on an option 5 for a report and option 6 for display of relevant test weight. In addition, scoring threshold 7 may be displayed to indicate the desirability of the applicant for a particular position such as job title 2. Time column 8 presents an estimate of the time elapsed. The bottom right portion of menu screen 1 presents similar entries for Aptitude Sub-tests 9. The test administrator can alter these recommended settings to tailor the test evaluations for the company's specific requirements.

FIG. 2 shows an introductory sample screen for a Vocabulary test. A professional voice actor speaks the directions 13 printed below. The subject is prompted with an auditory cue 14 such as "chair", upon which time he or she should click on the chair 15 picture. If he or she realizes that an error has been made, the repeat symbol 12 can be clicked to get a second try. Continuing with the audio 14, a sharpener 16 and a calculator 17 should be indicated.

A similarly administered test, "Information," is shown in the screen image of FIG. 3, wherein Audio instructions 21 are presented. Then audio statements 22 are presented and the tested subject is to indicate the image of the item which answers the question such as eye 24, nose 23 or teeth 25. Button 20 can be clicked to correct an answer.

FIG. 4 shows a screen image of a Categorization test. As per audio instructions 27, the objective is to select the picture of the item which is not like the others. Audio statements 28 would only be given during sample questions. In this case, the picture of the lion 29 is the correct answer.

FIG. 5 is a screen image of a sample question from a Social Apperception test. Audio instructions 33 define the objective as to "choose the person that goes with what you heard". Button image 32 can be clicked to change an answer. Sample statement 34 goes with image 35 since the statement displays anger.

FIG. 6 shows a screen from an Auditory Memory test. Audio directions 38 and examples 39 are strictly an introduction. The actual test presents a stream of numbers using audio. The subject has to enter the digits in the same order by clicking on number symbols 40. He or she may click cancel button 41 to try again, or signal OK 42 if he or she feels his or her answer was the correct sequence.

FIG. 7 is a sample introductory screen from an Auditory Memory with Visual Distractions. The audio instructions, 45 and 46, explain the added visual "clutter" 43 consisting of 3-D images of spheres surrounding the numeric display 40. The test begins as the sequences 47 are read on the audio stream.

Visual Memory test audio directions 50 and 51 are shown in FIG. 8.

The corresponding screen image is shown in FIG. 9. Shapes are presented in a sequence one at a time in frame 52. The subject has to click on the shape images continuously displayed in the same order and then click OK 56 when done. The subject can change his answer once by first pressing CANCEL 55. In the case shown, the image shown in frame 52 is the same shape as item 53 below. Audio instructions 54 comment on the answer of the subject, and give instructions for further proceedings.

FIG. 10 is a screen image of a Visual Closure test. Basic audio instruction 60 is presented for this sample. Explanation 61 is also for illustration. The object image 63 emerges as more of random background 62 is converted to image 63 in a progressive fashion. When the subject recognizes the picture as one of the four choices 64 presented, he or she clicks on the matching image. This is a very smooth operation, and the time to answer is accurately noted by the computer.

Figure 11A:
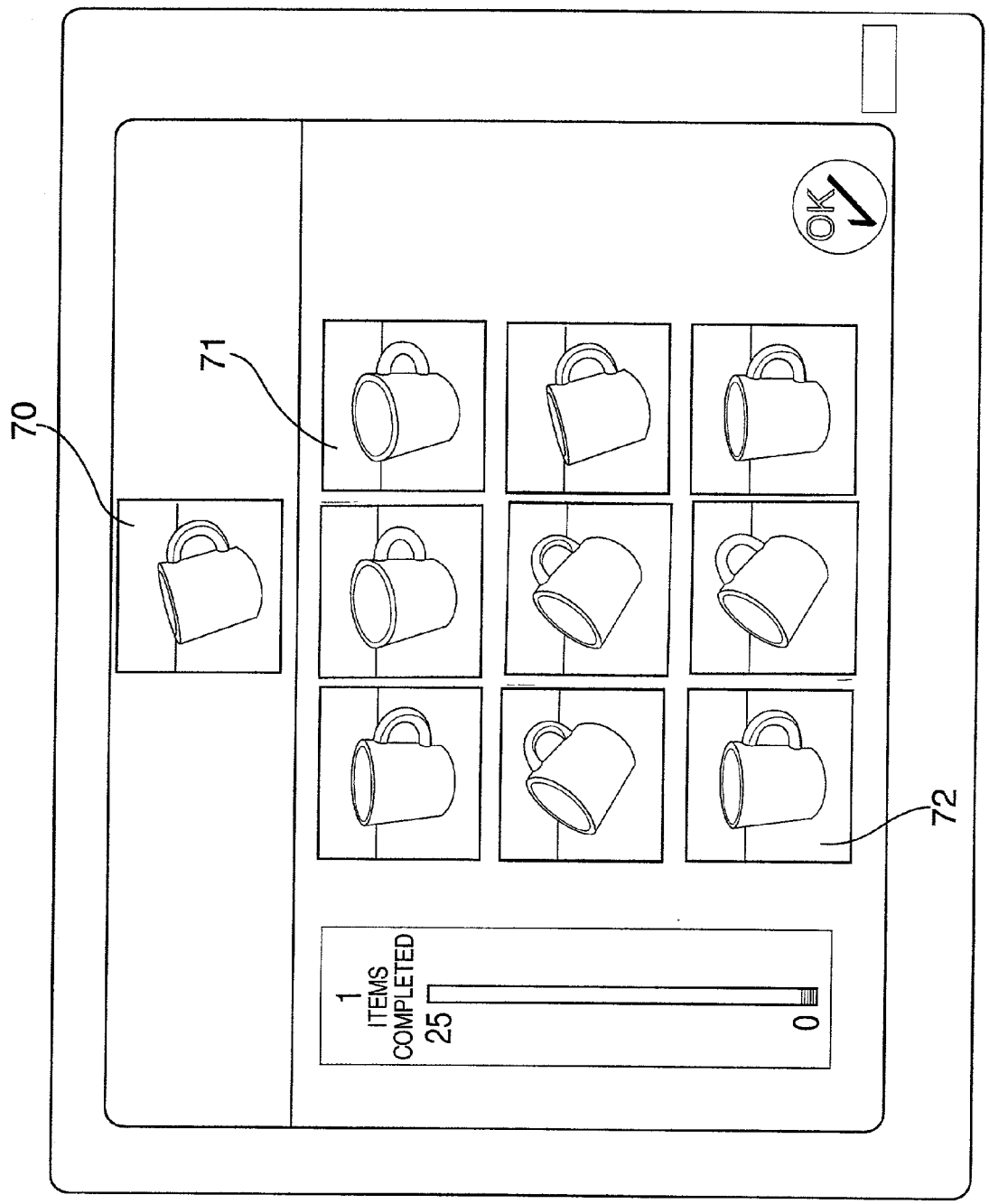
FIGS. 11A, 11B, 11C, 11D, 11E, 11F and 11G show various sample screen images for a Stress Tolerance Test thereof.
Figure 11B:
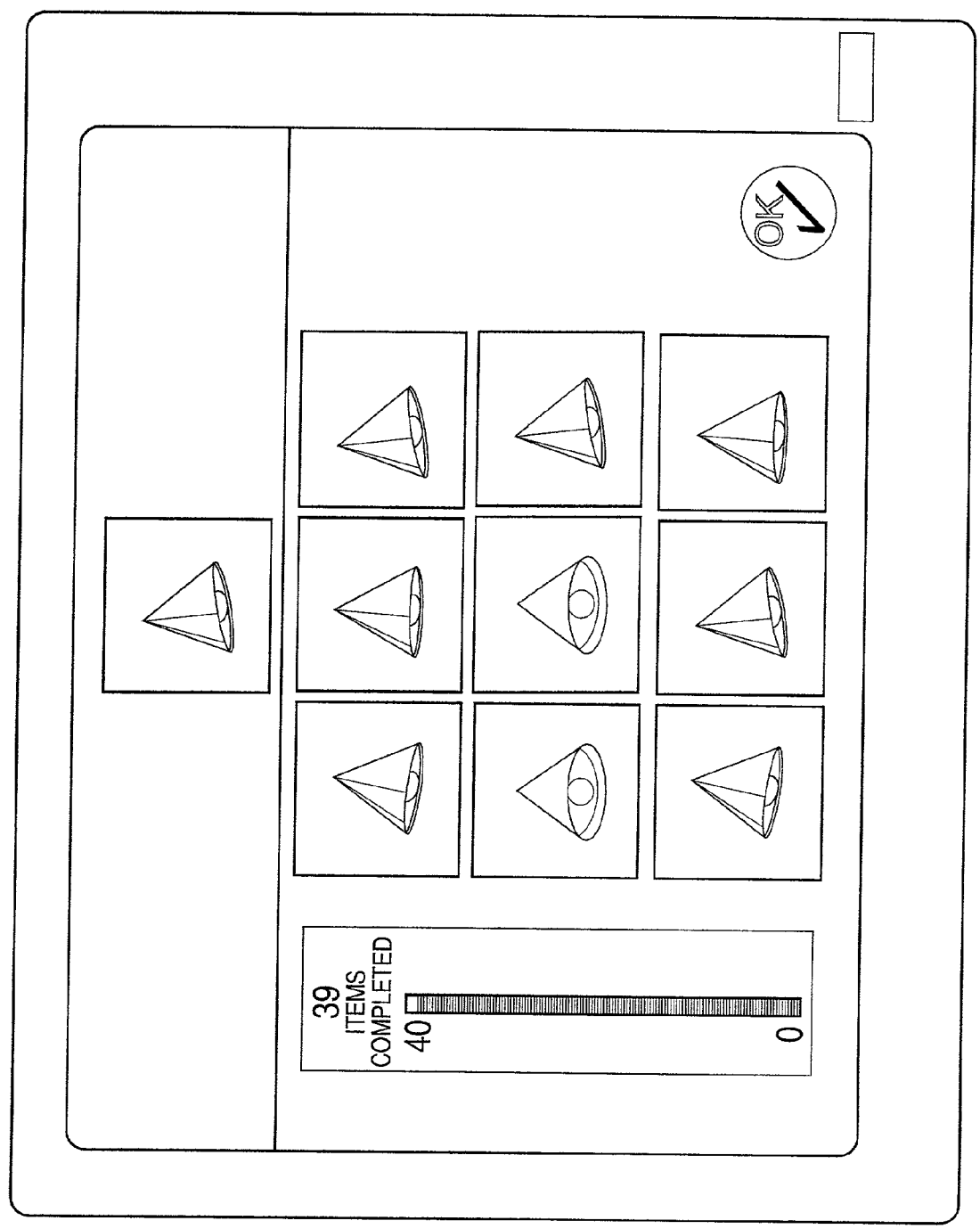
Figure 11C:
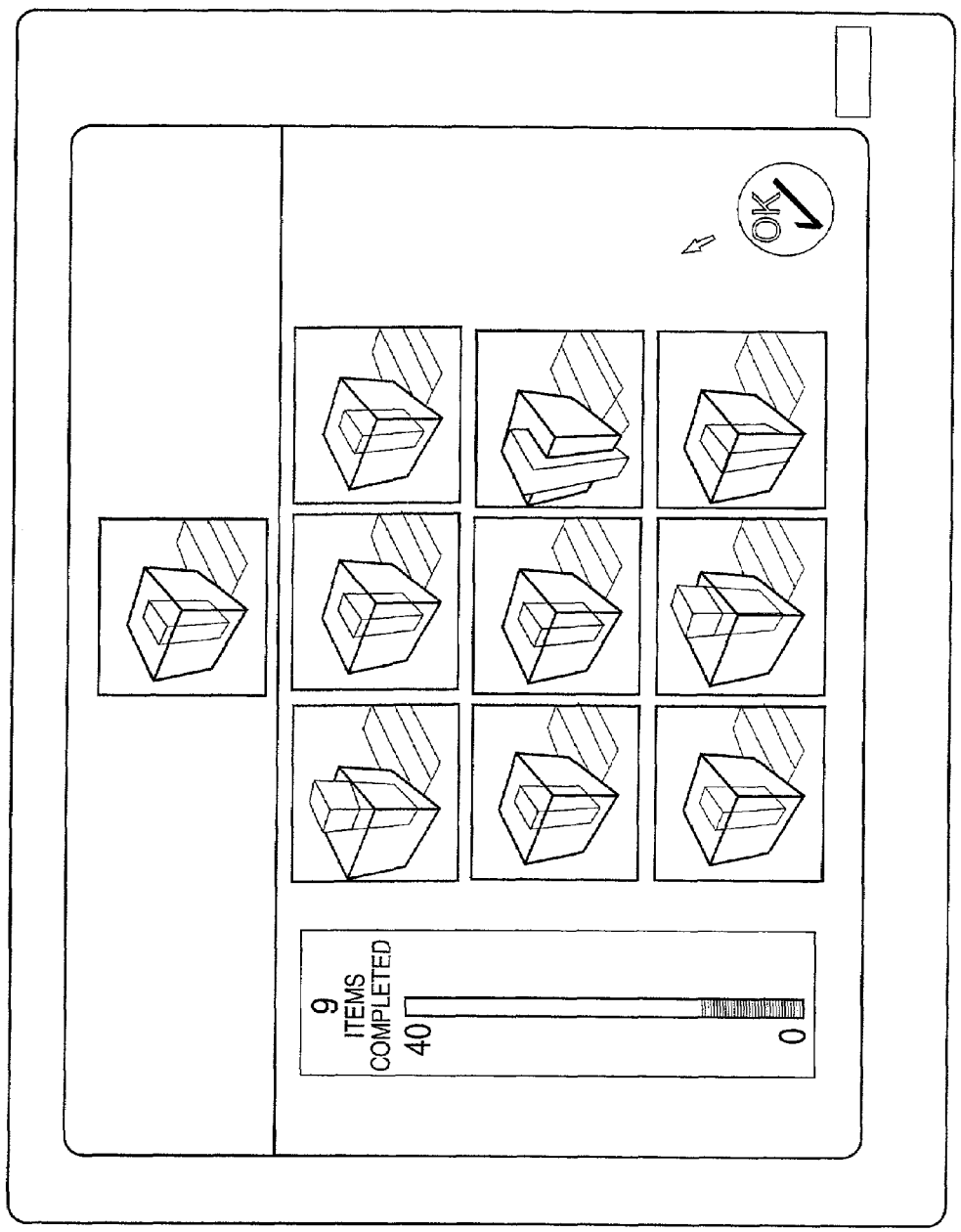
Figure 11D:
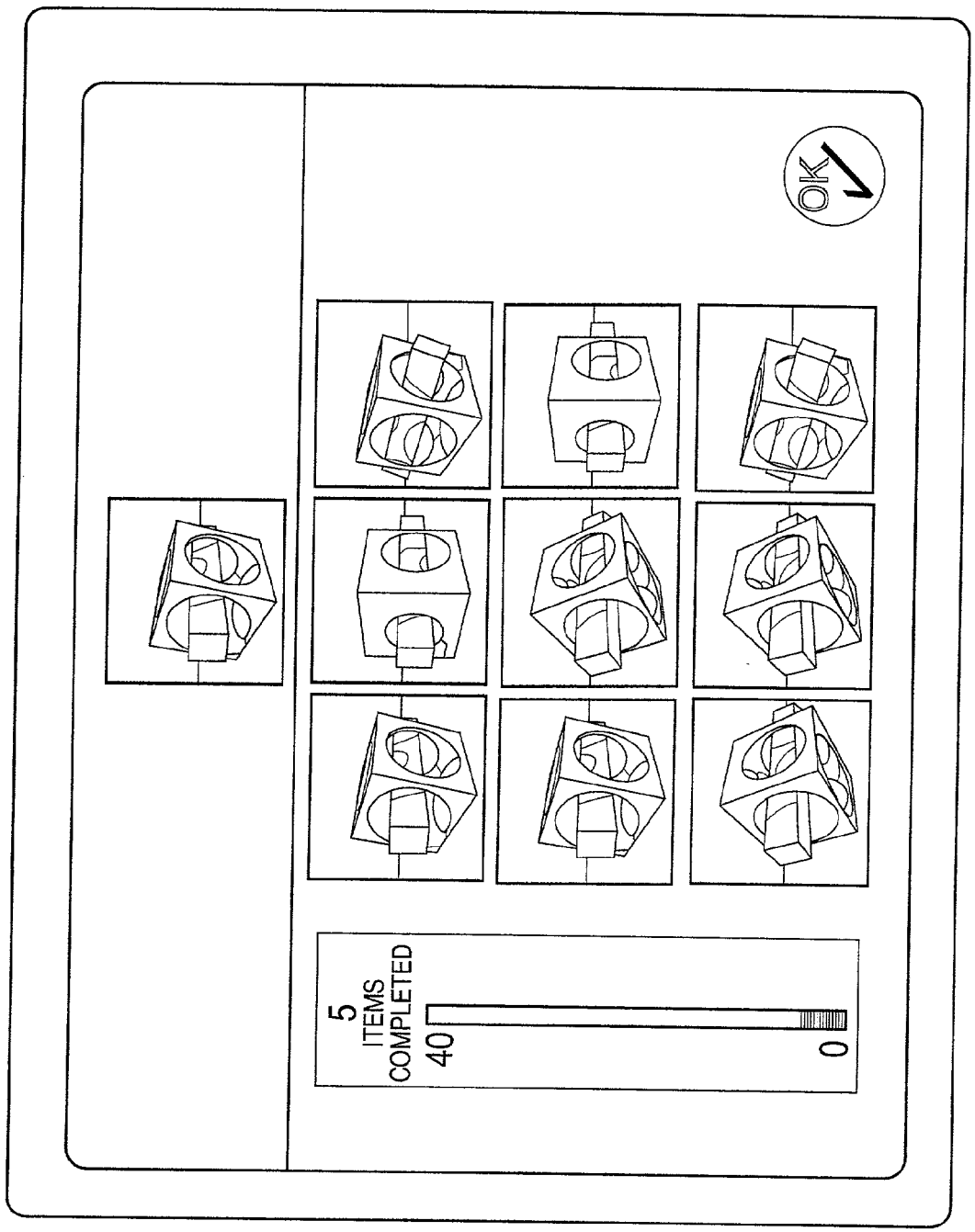
Figure 11E:
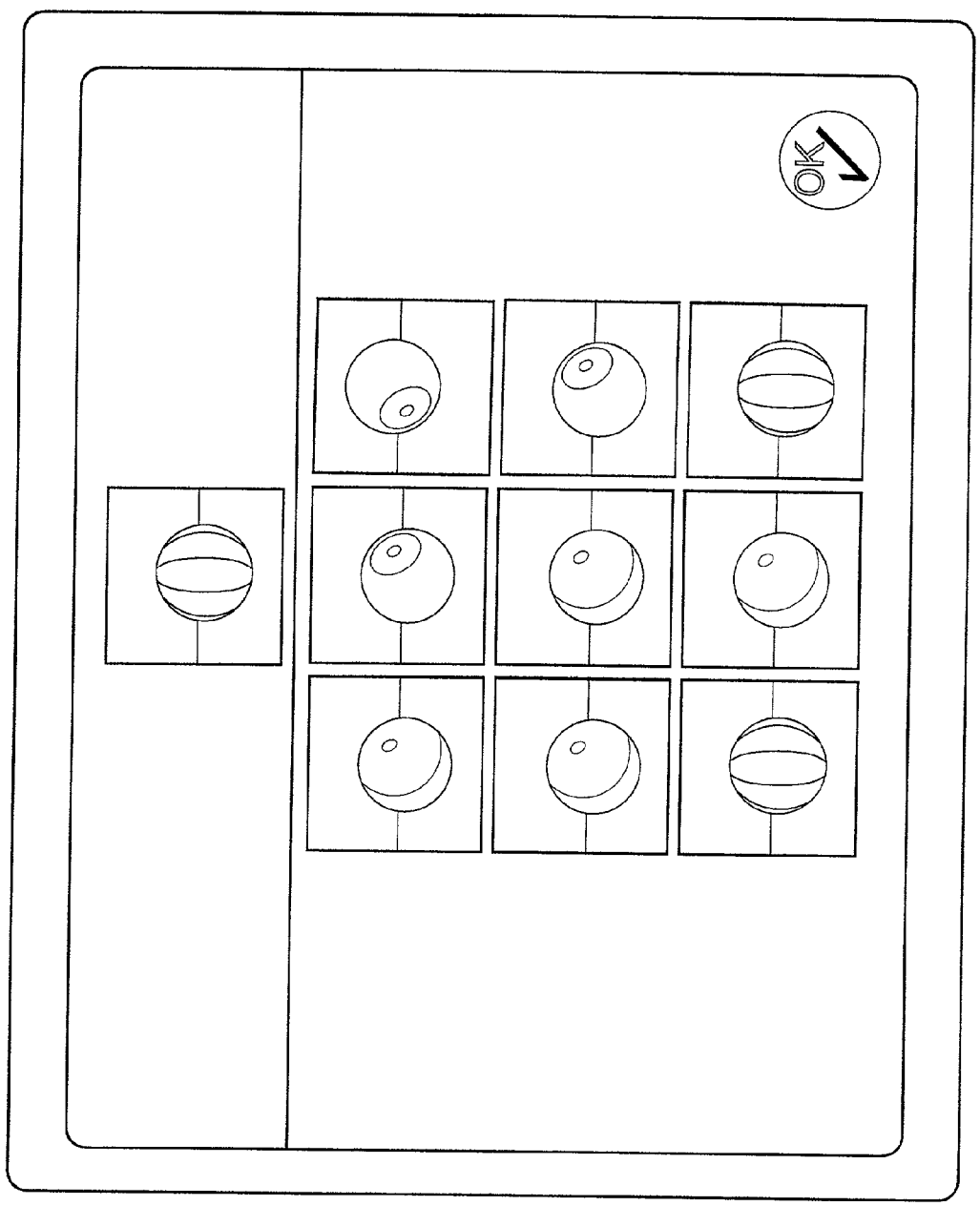
Figure 11F:
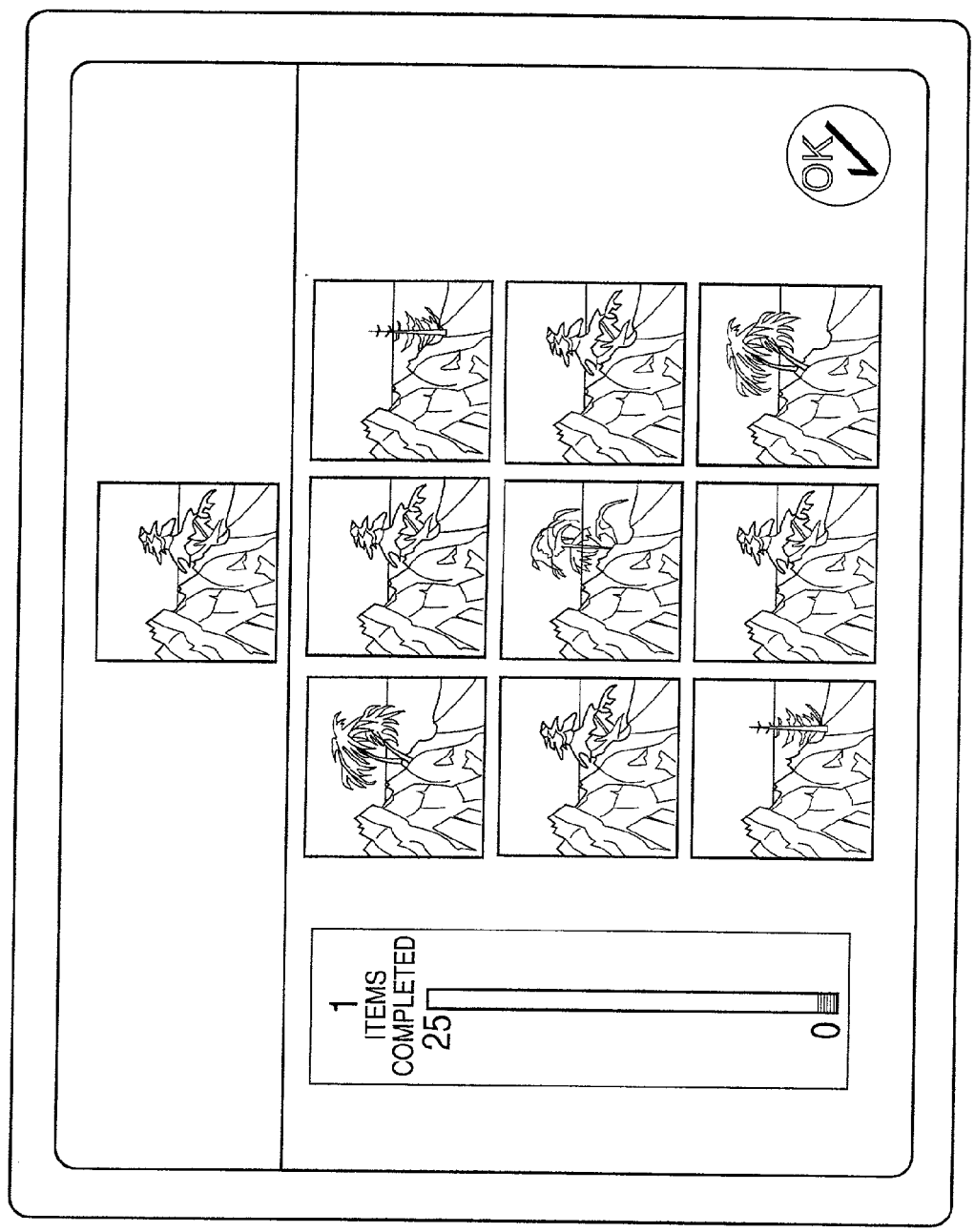
Figure 11G:
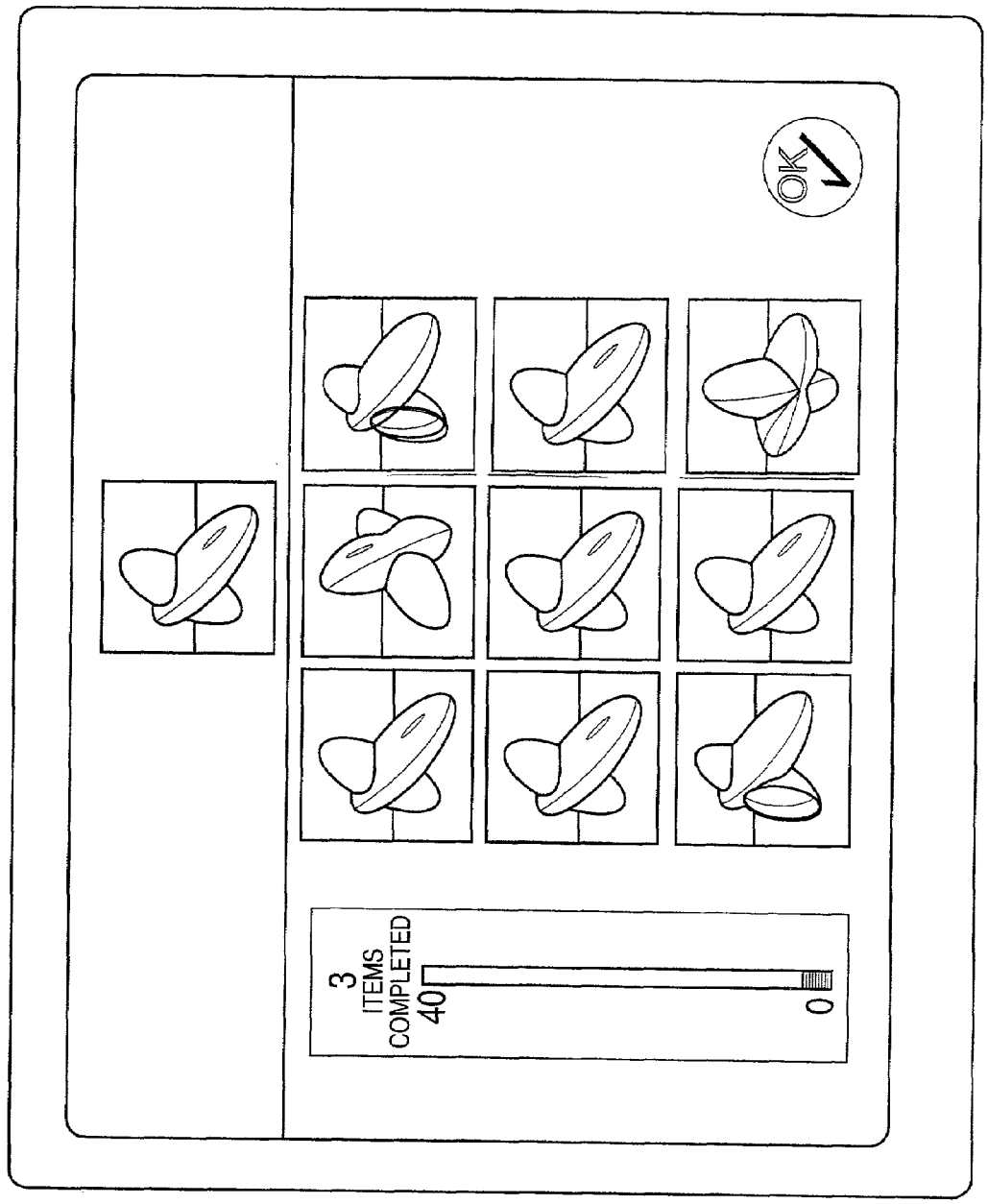

FIGS. 11A, 11B, 11C, 11D, 11E, 11F and 11G show various sample screen images for a Stress Tolerance Test thereof. For example, FIG. 11A shows a picture of an object 70, which is presented in a single panel on top. One or more exactly matching images are in the set of nine image panels below. In this example of FIG. 11A, panels 71 and 72 match the upper image exactly. The object is to find all matches and click on them in a short period of time. FIGS. 11B, 11C, 11D, 11E, 11F and 11G show other configurations for matching similar images together.

FIG. 12A shows some introductory audio instructions. No stress is provided yet. By the time of the last set of audio instructions, stress inducing commands are introduced, such as reducing the time factor in which to answer a question, and the introduction of verbal chiding, compelling the person being tested to work faster than has been previously done, along with other optional stress-inducing visual or auditory sound effects, such as flashing lights or alarming music.

The audio of FIG. 12B illustrates the stress introduced by the auditory portion of the Stress Tolerance Test.

Figure 13A:
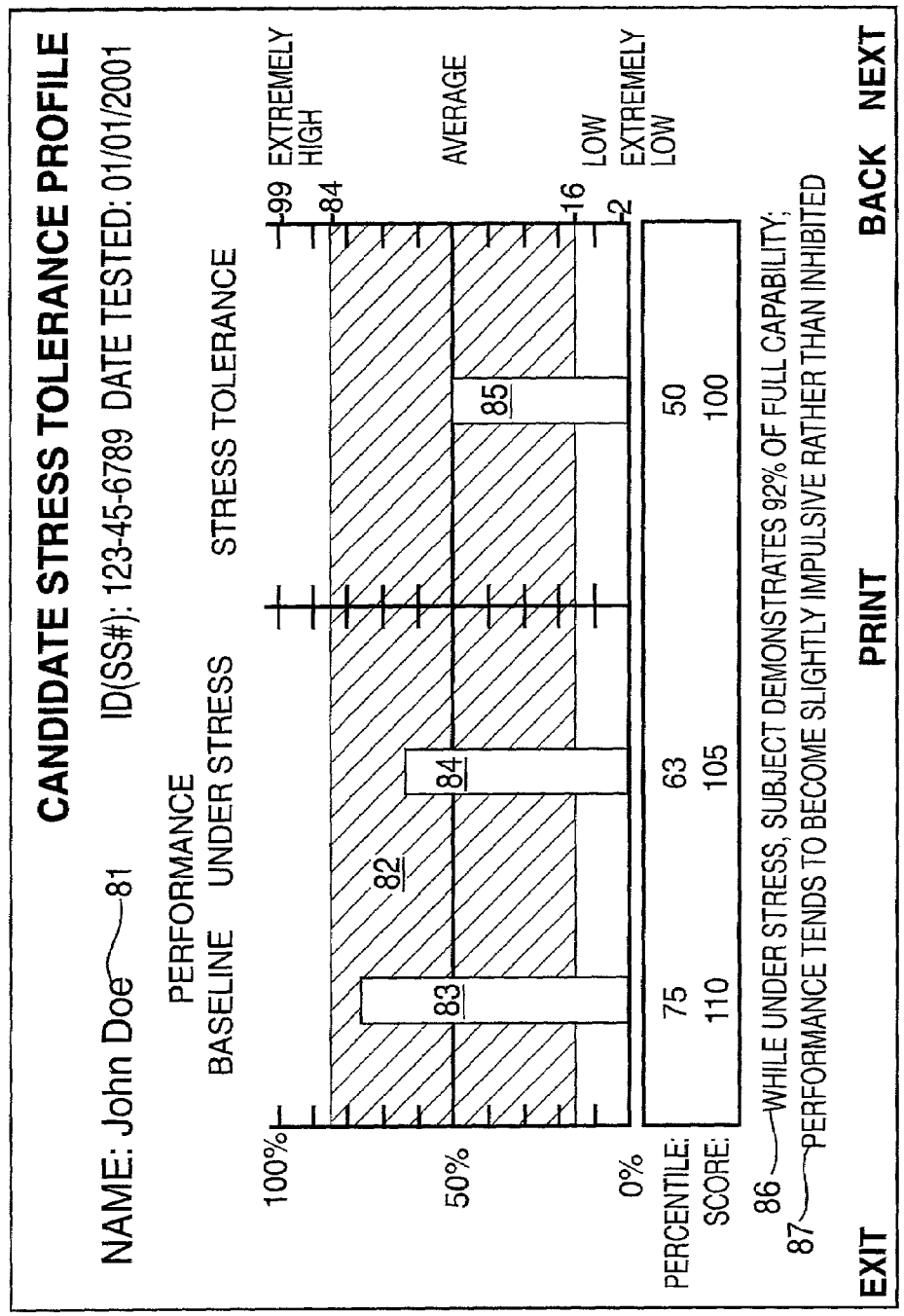
FIG. 13A shows a performance results screen for a Stress Tolerance Test thereof.

FIG. 13A shows a Performance Results screen presentation 80 for the Stress Tolerance Test. For example, FIG. 13A represents the results of the Stress Module in relation to the subject examinee 81 himself or herself and in relation to a general pool of examinees. The wide shaded bar 82 that extends across the entire graph is the measure of the average performance of the general pool of examinees. This Stress Test Module uses sensory indicia to simulate a stressful working environment involving deadlines, accuracy, time urgencies, and negative feedback. The first bar 83 on the left designated as "Baseline Performance", together with the percentile and raw score below it, indicates the level of the performance of subject examinee 81 when tested in a non-stressful environment, calm environment.

The second bar 84, when the graph is viewed from left to right, designated as "Performance Under Stress", together with the percentile and raw score underneath it, indicates the level of the performance of subject examinee 81 when tested under stressful conditions.

The third bar 85, when the graph is viewed from left to right, designated as "Stress Tolerance Index", together with the percentile and raw score below it, indicates the level of change in the performance of subject examinee 81 between testing with stressful conditions and with non-stressful baseline conditions.

The first line of text 86 under the graph indicates the positive performance of the examinee in relation to his own performance.

The second line of text 87 under the graph indicates the pattern of error of subject examinee 81. This error pattern is analyzed and reported as either impulsive or inhibited and then is weighed as "slight", "moderate" or "significant".

FIG. 13B shows a screen image of an example of the biofeedback monitoring used in conjunction with the Stress Tolerance Test. While FIG. 13B shows that the data is manually inputted, it is known that alternatively the data may be automatically inputted from the sensors and recorded automatically to the system.

Figure 13C:
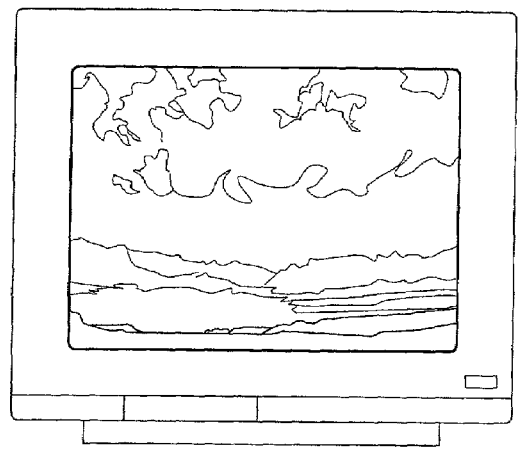
FIGS. 13C, 13D and 13E show various relaxation phase screens following a Stress Tolerance Test thereof.
Figure 13D:
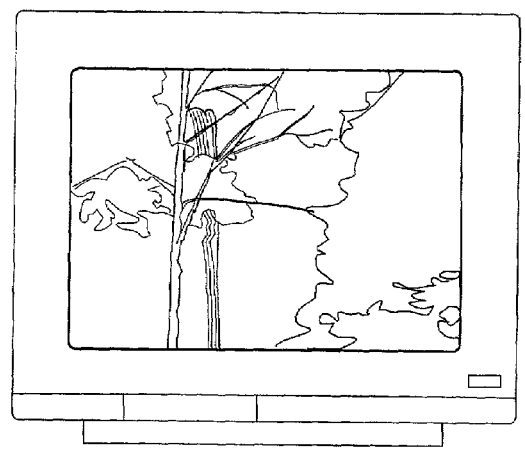
Figure 13E:
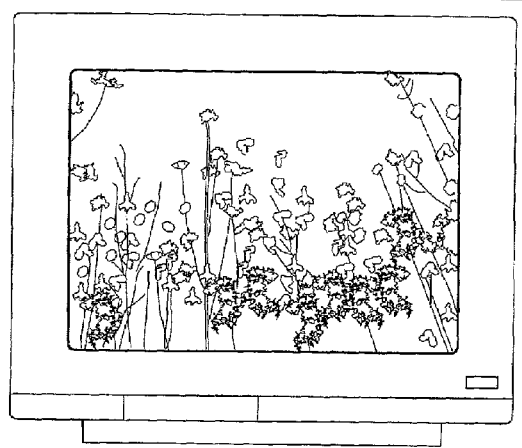

During this time, as shown in FIGS. 13C, 13D and 13E, a "slide show" relaxation phase of non-stressful scenes, such as landscapes, is presented to the subject on the computer screen.

FIG. 14 shows a part of a sequence of sample questions with multiple-choice answers from a sample Integrity test. Some questions form related subject matter and these subsets are dispersed. For example, questions 32 and 36 are part of a Drug subset 95. Questions 35 and 40 are part of a Bribery subset 97. As noted above in the "Background of the Invention" portion, it has been found previously in the prior art, primarily from testing on polygraph tests, that questions that take longer to answer and that exhibit more response time latency variability are not being answered truthfully. The Integrity test uses this general principle in sophisticated algorithms comparing responses to similar questions to flag false answers.

Figure 15:
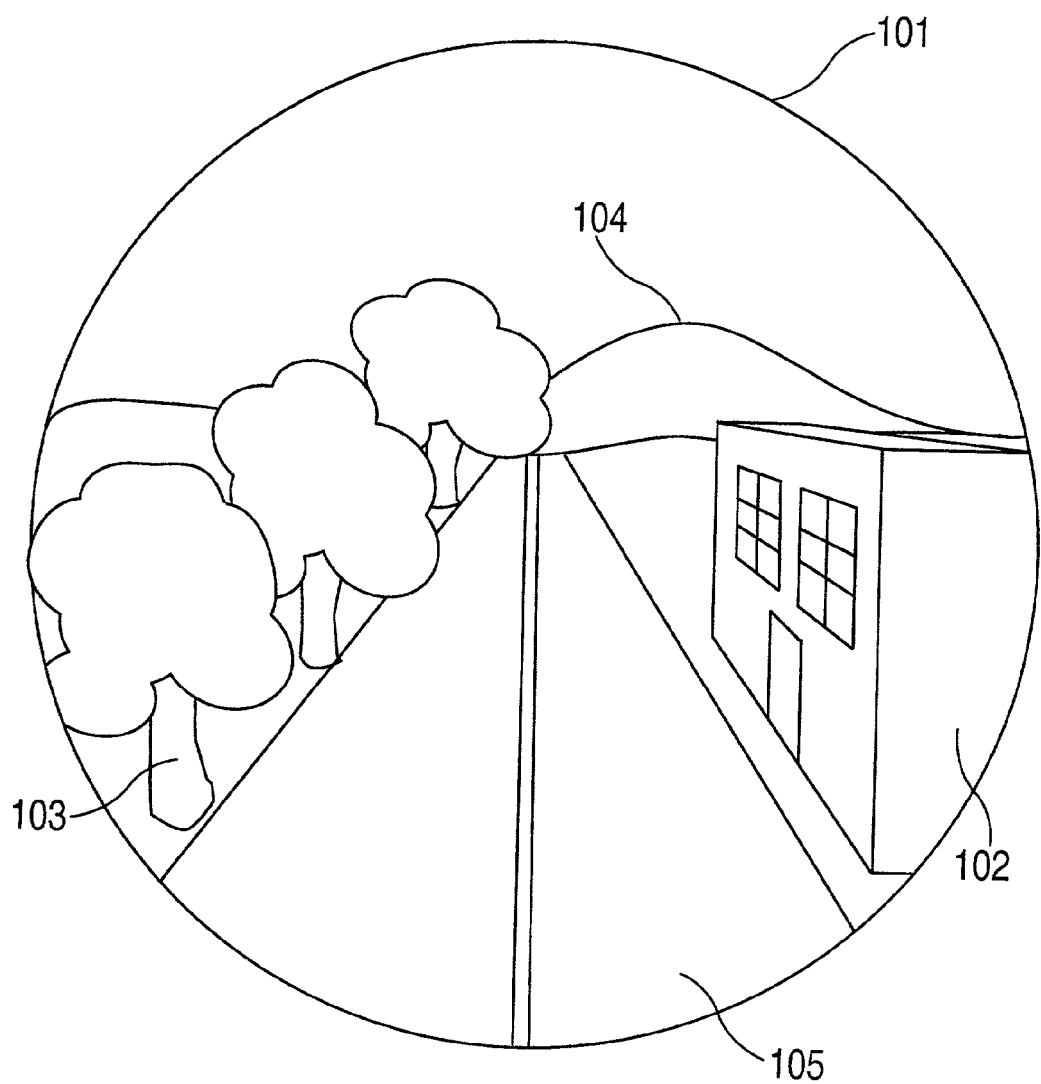

FIG. 15 shows a screen image for a virtual reality depiction of a work environment. For example, FIG. 15 is one image of a virtual reality simulation of actual outdoor working tasks of a land surveyor. In FIG. 15, a personal being assessed as a land surveyor views a simulated landscape scene to be measured, as seen through lens 101 of a land surveyor's transiting theodolite sighting telescope. The person being assessed sees a virtual depiction of an actual landscape scene, including man-made structures 102, such as buildings, natural structures, such as trees and a horizon 104 in the distance. A typical road 105 is depicted in actual perspective, so that the person being assessed can be assessed doing virtual simulations of actual land surveyor's tasks. Persons being assessed can be tested for their endurance under challenging conditions. For example, for a maritime surveyor, swaying of a seagoing boat can be provided in virtual reality images.

OPERATION OF THE INVENTION

The present invention utilizes a Computer Optimized Multimedia Intelligence Test (C.O.M.I.T.). The C.O.M.I.T. is an individually administered multi-subtest battery based on the Horn-Cattell model of fluid and crystallized intelligence. It yields a comprehensive, valid and reliable composite measure of general intelligence, as well as fluid and crystallized IQ scores. In the Horn-Cattell model, fluid intelligence refers to an individual's ability to devise and apply problem-solving strategies when faced with novel or unusual tasks. Fluid Intelligence reflects the individual's ability to be flexible and apply age-appropriate concept formation, analysis-synthesis and hypothetical-deductive reasoning to solve unfamiliar problems. Fluid intelligence is not heavily influenced by formal school experiences or cultural settings.

Crystallized intelligence, on the other hand, refers to applying knowledge and skills acquired through formal, school related learning experiences to a current problem. It is heavily influenced by culture, and taps word knowledge, verbal concept formation, categorizations and factual knowledge.

The C.O.M.I.T. is an appropriate measure of intelligence for any applied or clinical sheeting requiring assessment of intellectual abilities. The C.O.M.I.T. is flexible and allows for everything from a quick screening to a comprehensive assessment. The C.O.M.I.T. comes in many languages. It has excellent reliability and validity, and correlates significantly with existing measures of intelligence. Since it is both administered and scored by computer, human error and bias introduced by the examiner are eliminated from the testing process.

The C.O.M.I.T. test is computer administered, using high-end graphics and professional voice actors. The C.O.M.I.T. yields standard scores (scores with means equal to 100 and standard deviations of 15) for three scales: Composite IQ, Fluid IQ and Crystallized IQ. This permits direct comparisons with global scores earned on numerous measures of achievement such as the Wechsler series of intelligence tests.

The C.O.M.I.T. has a total of 12 sub-tests each producing standard scores (Mean=10; SD=3). Sub-tests that measure fluid intelligence are: Visual Analogies, Visual Closure, Visual Memory, and Auditory Memory. Sub-tests that measure crystallized intelligence are: Vocabulary, Information, and Categorization. The five supplemental scales are: Processing Speed, Social Apperception, Auditory Memory with Visual Distraction, Auditory Memory with Auditory Distraction, and Visual Memory with Auditory Distraction.

The selection of which sub-tests to administer during a testing session can be completely controlled. The evaluator has the following broad options:

Administer a Screening Battery, consisting of 4 reliable sub-tests and requiring 15–20 minutes to complete.

Administer a more comprehensive Standard Battery containing 7 sub-tests and requiring 25–30 minutes to complete.

Administer a customized test battery by selecting any or all of the 12 sub-tests.

The five supplemental sub-tests not included in either the Standard or the Screening battery requires and additional 3–5 minutes each to administer. Testing may be discontinued between sub-tests and continued at a later time.

Composite, Fluid and Crystallized IQ scores are presented in colorful graphic displays. Percentile scores are also presented for these composite scores. Graphs displaying performance on individual sub-tests show scaled scores, as well as percentile scores for each sub-test so that subject performance on each individual task can be measured relative to the normative sample. In addition, a special sub-test scatter score uses sophisticated algorithms to calculate sub-test scatter and summarize the individual's relative strengths and weaknesses compared to their own ipsative mean and overall performance. Percentile scores for sub-test performance are also displayed. All sub-test scores (including supplemental sub-test scores) are presented in colorful bar graphs that allow for clear visual comparisons of performance. In addition, supplemental sub-tests involving distraction yield a Distraction Index that indicates the degree to which an individual's performance was affected by distraction, as well as a visual depiction of which distracting modality proved most troublesome for the subject.

While other computer systems may be used, the preferable minimum system requirements are:

IBM compatible PC

486 Processor (Pentium recommended)

8 megabytes of RAM (16 Meg or more recommended)

16 bit sound card

CD-ROM drive 16-bit Color VGA graphics

The present invention also uses a Stress Tolerance Rapid Evaluation Software System (S.T.R.E.S.S.).

The ability to remain task focused under pressure is a critical component of successful performance across a wide spectrum of endeavors.

The Stress Tolerance Rapid Evaluation Software System (STRESS) is specifically designed to help psychologists and other professionals rapidly evaluate a subject's ability to remain task focused under stressful conditions. It provides a complete picture of the effects of stress on a subject's ability to sustain attention, maintain attention to detail and stay focused on task completion.

The STRESS test has wide applicability across diverse areas of practice, ranging from clinical to applied settings. It is unique and extremely precise because it directly measures an individual's ability to stay task focused under stress, rather than attempting to infer it from what an individual is willing to reveal on a self-assessment questionnaire. Some potential uses for the STRESS test include:

Candidate screening for high-risk or high-stress jobs

Suitability for duty or -re-deployment evaluations when the ability to remain task focused is at issue Stress research where standardized, object measures are required Stress management assessment and treatment evaluation Most individuals can complete the STRESS test in approximately 15 minutes. The test compares a subject's performance on a visual matching task under two conditions: Non-stress and stress. In each condition, subjects are presented with up to 4 items. Each item consists of 3D computer-generated shapes: A target shape and nine potential matches. Subjects must identify all the shapes on the screen that are identical to the target. Items occurring in the same order during non-stress and stress conditions were specifically designed to have identical difficulty-levels. Care was taken to reduce ethnic bias and keep the shapes culture-free. Conditions for producing stress were developed in consultation with experts in the field and specifically designed to induce autonomic nervous system arousal and a sense of time urgency. Professional voice actors do all the voice-overs.

For non-stress and stress conditions the following data are reported:

The number of items completed during that condition (max=40)

The average amount of time required for completing each item

Since non-stress and stress items are of identical difficulty, comparisons are made between the items completed during the stress condition and corresponding non-stress items. These comparisons are:

The total number of correct matches during each condition

The total number of errors of omission or missed opportunities for matches

The total number of commission or incorrect matches during each condition

The non-stress and stress difference scores for correct matches, errors of omission and errors of commission Examination of the difference-scores from the STRESS test provides a precise indication as to the degree to which an individual is affected by stress, as well as an analysis of the subject's tendency to make errors of commission or errors of omission under pressure.

The STRESS test is administered and scored by computer thus eliminating human error introduced by variations in test administration and scoring.

While other computer systems may be used, the preferable minimum system requirements are:

IBM compatible PC

486 Processor (Pentium recommended)

8 megabytes of RAM (16 Meg or more recommended)

16 bit soundcard

CD-ROM drive 16-bit Color VGA graphics

It is further noted that other modifications may be made to the present invention, without departing from the scope of the invention, as noted in the appended claims.

I claim:

1. A personnel evaluation system comprising:
   at least one multimedia computer for transceiving audio and visual stimuli for a subject;
   a storage memory of said system for storing application modules;
   at least one central processing unit within said multimedia computer to administer said application modules to said subject, perform analysis of input data, and cause said multimedia computer to transmit said stimuli;
   said application modules comprising at least one software application for utilizing multimedia technology to assess in a clinically valid manner respective skills and abilities of the subject which cannot be assessed by non-multimedia test content, said skills and abilities applicable to work-related tasks;
   a software application in which stimuli are revealed progressively to a subject and the subject identifying the emerging stimuli as early as he or she can to determine the precise level of detail required by the subject to correctly identify the stimuli, the identification made by the subject being evaluated; and
   wherein said storage memory of said system includes a scoring system derived from database statistics calculated for a representative sample of a specific population of subjects being tested and a predetermined pass/fail threshold for each said application module based on updated database statistics reflecting past test results of prior subjects in a similar job role or in a role requiring similar skills or abilities.

2. The evaluation system of claim 1 in which a subject's performance on a specific task is compared under non-stressful and stressful conditions.

3. The evaluation system of claim 1 including a social perception test in which pictures of people in a variety of postures, facial expressions, and interactions are displayed and an audio presentation of a spoken statement is made, said subject identifying the picture of the person or people most likely to have made that statement or most closely associated with that statement.

4. The evaluation system of claim 1 in which said system moves on to easier sets of questions or more difficult sets of questions when the subject makes a predetermined number of incorrect answers or a predetermined number of correct answers.

5. The evaluation system of claim 1 wherein said system records an answer of a subject to a particular question during a test, updates a test score and dynamically routes subsequent questions in a logical flow to a subject depending upon the correctness or incorrectness of the subject's answer to said particular question, said dynamic routing progressing through said test to provide subsequent questions to the subject depending upon the subject's responses on prior questions of said test to estimate the subject's abilities and dynamically determine the most appropriate starting point and difficulty level of subsequent questions of the test for that subject.

6. The evaluation system of claim 1 in which transmission of said stimuli includes transmission via the internet or a company intranet.

7. A personnel evaluation system comprising:
   a multimedia computer for transceiving audio and visual stimuli for a subject;
   a storage memory of said system for storing application modules utilizing multimedia technology to assess skills and abilities in a manner which cannot be assessed by non-multimedia content or utilizing multimedia technology to measure skills or abilities applicable to work-related tasks in a manner which is more clinically valid than the manner in which such skills or abilities must be measured when using only non-multimedia, text-based content;

a central processing unit within said multimedia computer to administer said application modules to said subject, perform analysis of input data, and cause said multimedia computer to transmit said stimuli;

said application modules comprising a software application to complete at least one of the following tasks: to store and evaluate all input data, simulate work-related tasks, deliver stress-inducing audio or visual stimuli to said subject, said stress-inducing audio or visual stimuli being race, gender, ethnic, and cultural neutral, to interact with said subject, and assess at least one of the intelligence, interest, values, emotional status, mental health, neurological impairment, education, social skills, aptitude, processing speed, performance efficiency, task focus, distractability resistance, stress-tolerance, communication skills, knowledge, reasoning ability, logic skills, job skills, vocabulary, emotional quotient (EQ), impulsivity, risk-tolerance level, personality and specific approach to problem solving;

a software application in which stimuli are revealed progressively to a subject and the subject identifying the emerging stimuli as early as he or she can to determine the precise level of detail required by the subject to correctly identify the stimuli, the identification made by the subject being evaluate;

wherein said storage memory of said system includes a scoring system derived from database statistics calculated for a particular job title, incorporating a suggested default list of application modules to be administered for a specific job title, a suggested weight and signification applied to each said application module score in an overran suitability to job title score, and a predetermined pass/fail threshold for each said application module based on updated database statistics reflecting past test results of prior subjects in a similar job role;

wherein said system incorporates the ability to compare a subject's performance on a task under non-stressful and stressful conditions to determine a subject's stress tolerance level;

wherein said stressful conditions incorporates multimedia stressors using one or more of the following: stressful music, stressful audio, negative feedback, and restricted time deadlines for task completion;

wherein said system incorporates error pattern analysis so as to determine not just the degree to which a subject is affected by stress, but in what manner the subject tends to become affected and in what manner his performance is most likely to change when placed in a stressful environment; and wherein said system incorporates the ability to automatically stop administration of remaining application modules of said application modules, in the event that the subject's performance is below a predetermined pass/fail threshold for any particular application module of said application modules.

8. A personnel evaluation system comprising:

at least one multimedia computer for transceiving audio and visual stimuli for a subject from at least one of a hard drive of said computer, or the Internet, or a company intranet, or combination thereof;

a storage memory of said system for storing application modules;

at least one central processing unit within said at least one multimedia computer to administer said application modules to said subject; perform analysis of input data, and cause said multimedia computer to transmit said stimuli;

said application modules comprising at least one software application to complete at least one of the following tasks: to store and evaluate all input data, simulate work-related tasks, deliver stress-inducing audio or visual stimuli to said subject, said stress-inducing audio or visual stimuli being race, gender, ethnic, and cultural neutral, to interact with said subject, and assess at least one of the intelligence, interest, values, emotional status, mental health, neurological impairment, education, social skills, aptitude, processing speed, performance efficiency, task focus, distractability resistance, stress-tolerance, communication skills, knowledge, reasoning ability, logic skills, job skills, vocabulary, emotional quotient (EQ), impulsivity, risk-tolerance level, personality and specific approach to problem solving;

a software application in which stimuli are revealed progressively to a subject and the subject identifying the emerging stimuli as early as he or she can to determine the precise level of detail required by the subject to correctly identify the stimuli, the identification made by the subject being evaluated;

wherein said storage memory of said system includes a scoring system derived from database statistics calculated for a particular job title, incorporating a suggested default list of application modules to be administered for a specific job title, a suggested weight and signification applied to each said application module score in an overall suitability to job title score, and a predetermined pass/fail threshold for each said application module based on updated database statistics reflecting past test results of prior subjects in a particular job role or similar job role; and wherein when a scoring ceiling or basal threshold is reached when the subject misses a predetermined number of a consecutive correct answers or answers a predetermined number of consecutive questions correctly in said tests, said system dynamically adapting by automatically moving on to easier or more difficult sets of questions being presented to the subject.

9. A personnel evaluation system comprising:

at least one multimedia computer for transceiving audio and visual stimuli for a subject from at least one of a hard drive of said computer, or the Internet or a company intranet, or combination thereof;

a storage memory of said system for storing application modules;

at least one central processing unit within said at least one multimedia computer to administer said application modules to said subject, perform analysis of input data, and cause said multimedia computer to transmit said stimuli;

said application modules comprising at least one software application for doing at least one of the following tasks: utilizing multimedia technology to assess skills and abilities in a clinically valid manner, or utilizing multimedia technology to assess skills or abilities applicable to work-related tasks in a more effective manner than how those skills or abilities can be assessed by non-multimedia content or utilizing multimedia technology to compare the performance of a subject on a specific task with distractions present to the performance of the same subject on the same or similar task without distraction present, in a more effective manner than can be assessed when utilizing non-multimedia content or utilizing multimedia technology to compare the performance of a subject on a specific task when under stressful conditions to the same subject's performance on the same or a similar task when under less stressful or non-stressful conditions, in a more effective or real life manner than can be assessed by utilizing non-multimedia content or utilizing multimedia technology to assess the social skills of a subject using audio and facial expressions or social interactions, in a more effective manner than can be assessed by utilizing non-multimedia content, or combinations thereof;

a software application in which stimuli are revealed progressively to a subject and the subject identifying the emerging stimuli as early as he or she can to determine the precise level of detail required by the subject to correctly identify the stimuli, the identification made by the subject being evaluated; and wherein said storage memory of said system includes a scoring system derived from database statistics calculated for a representative sample pf a specific population being tested and a predetermined pass/fail threshold for each said application module based on updated database statistics reflecting past test results of prior subjects in a similar job role.

10. A personnel evaluation system comprising:

at least one multimedia computer for transceiving audio and visual stimuli for a subject from at least one of a hard drive of said computer, or the Internet or a company intranet, or combination thereof;

a storage memory of said system for storing application modules;

at least one central processing unit within said multimedia computer to administer said application modules to said subject, perform analysis of input data, and cause said multimedia computer to transmit said stimuli;

said application modules comprising at least one software application for doing at least one of the following tasks: utilizing multimedia technology to assess skills and abilities in a clinically valid manner or utilizing multimedia technology to assess skills or abilities applicable to work-related tasks in a more effective manner than how those skills or abilities can be assessed by non-multimedia content or utilizing multimedia technology to compare the performance of a subject on a specific task with distractions present to the performance of the same subject on the same or similar task without distraction present, in a more effective manner than can be assessed when utilizing non-multimedia content or utilizing multimedia technology to compare the performance of a subject on a specific task when under stressful conditions to the same subject's performance on the same or a similar task when under less stressful or non-stressful conditions, in a more effective or real life manner than can be assessed by utilizing non-multimedia content or utilizing multimedia technology to assess the social skills of a subject using audio and facial expressions or social interactions, in a more effective manner than can be assessed by utilizing non-multimedia content, or combinations thereof;

a software application in which stimuli are revealed progressively to a subject and the subject identifying the emerging stimuli as early as he or she can to determine the precise level of detail required by the subject to correctly identify the stimuli, the identification made by the subject being evaluated;

wherein said storage memory of said system includes a scoring system derived from database statistics calculated for a particular job title, incorporating a suggested default list of application modules to be administered for a specific job title, a suggested weight and signification applied to each said application module score in an overall suitability to job title score, and a predetermined pass/fail threshold for each said application module based on continually updated database statistics reflecting past test results of prior subjects in a particular job role or similar job role; and wherein when a scoring ceiling or basal threshold is reached when the subject misses a predetermined number of a consecutive correct answers or answers a predetermined number of consecutive questions correctly in said tests, said system dynamically adapting by automatically moving on to easier or more difficult sets of questions being presented to the subject.

11. A personnel evaluation system comprising:

at least one multimedia computer for transceiving audio and visual stimuli for a subject from at least one of a hard drive of said computer, or the Internet or a company intranet, or combination thereof;

a storage memory of said system for storing application modules;

at least one central processing unit within said multimedia computer to administer said application modules to said subject, perform analysis of input data, and cause said multimedia computer to transmit said stimuli;

said application modules comprising at least one software application for doing at least one of the following tasks: utilizing multimedia technology to assess skills and abilities in a clinically valid manner or utilizing multimedia technology to assess skills or abilities applicable to work-related tasks in a more effective manner than how those skills or abilities can be assessed by non-multimedia content or utilizing multimedia technology to compare the performance of a subject on a specific task with distractions present to the performance of the same subject on the same or similar task without distraction present, in a more effective manner than can be assessed when utilizing non-multimedia content or utilizing multimedia technology to compare the performance of a subject on a specific task when under stressful conditions to the same subject's performance on the same or a similar task when under less stressful or non-stressful conditions, in a more effective or real life manner than can be assessed by utilizing non-multimedia content or utilizing multimedia technology to assess the social skills of a subject using audio and facial expressions or social interactions, in a more effective manner than can be assessed by utilizing non-multimedia content, or combinations thereof;

a software application in which stimuli are revealed progressively to a subject and the subject identifying the emerging stimuli as early as he or she can to determine the precise level of detail required by the subject to correctly identify the stimuli, the identification made by the subject being evaluated;

wherein said storage memory of said system includes a scoring system derived from database statistics calculated for a particular job title, incorporating a suggested default list of application modules to be administered for a specific job title, a suggested weight and signification applied to each said application module score in an overran suitability to job title score, and a predetermined pass/fail threshold for each said application module based on updated database statistics reflecting past test results of prior subjects in a similar job role;

wherein said system incorporates the ability to compare a subject's performance on a task under non-stressful and stressful conditions to determine a subject's stress tolerance level;

wherein said stressful conditions incorporates multimedia stressors using one or more of the following: stressful music, stressful audio, negative feedback, and restricted time deadlines for task completion;

wherein said system incorporates error pattern analysis so as to determine not just the degree to which a subject is affected by stress, but in what manner the subject tends to become affected and in what manner his performance is most likely to change when placed in a stressful environment; and wherein said system incorporates the ability to automatically stop administration of remaining application modules of said application modules, in the event that the subject's performance is below a predetermined pass/fail threshold for any particular application module of said application modules.

\* \* \* \* \*